United States Patent
Ruppino et al.

(10) Patent No.: US 12,234,277 B2
(45) Date of Patent: Feb. 25, 2025

(54) HYDROPHOBIC INTERACTION CHROMATOGRAPHY FOR VIRAL CLEARANCE

(71) Applicant: Regeneron Pharmaceuticals, Inc., Tarrytown, NY (US)

(72) Inventors: John Ruppino, Boonton, NJ (US); John Mattila, Nyack, NY (US); Robert Stairs, Wellborn, FL (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1074 days.

(21) Appl. No.: 17/150,973

(22) Filed: Jan. 15, 2021

(65) Prior Publication Data

US 2021/0221840 A1    Jul. 22, 2021

Related U.S. Application Data

(60) Provisional application No. 62/962,506, filed on Jan. 17, 2020.

(51) Int. Cl.
| | | |
|---|---|---|
| C07K 16/06 | (2006.01) |
| A61K 39/395 | (2006.01) |
| C07K 1/20 | (2006.01) |
| C12Q 1/70 | (2006.01) |
| G01N 30/06 | (2006.01) |
| G01N 30/34 | (2006.01) |

(52) U.S. Cl.
CPC ............. *C07K 16/065* (2013.01); *C07K 1/20* (2013.01); *C12Q 1/70* (2013.01); *G01N 30/06* (2013.01); *G01N 30/34* (2013.01)

(58) Field of Classification Search
CPC .......... C07K 16/065; C07K 1/20; C12Q 1/70; G01N 30/06; G01N 30/34
See application file for complete search history.

(56) References Cited

U.S. PATENT DOCUMENTS

| | | |
|---|---|---|
| 2012/0264920 A1 | 10/2012 | Wang et al. |
| 2016/0130339 A1 | 5/2016 | Hickman |
| 2019/0298829 A1 | 10/2019 | Wan et al. |

FOREIGN PATENT DOCUMENTS

| | | |
|---|---|---|
| WO | WO2010/048192 A2 | 4/2010 |
| WO | WO2016/118707 A1 | 7/2016 |

OTHER PUBLICATIONS

Li J.J. et al. "Monoclonal Antibody Aggregate Polishand Viral Clearance Using Hydrophobic Interaction Chromatography" Thermo Fisher Scientific, vol. 17, pp. 1-7, XP002802707, Nov.-Dec. 2019 (Year: 2019).*

Kjell O. Eriksson, "Chapter 19—Hydrophobic Interaction Chromatography." Biopharmaceutical Processing, edited by Günter Jagschies, Eva Lindskog, Karol Łącki, and Parrish Galliher. Elsevier, 2018, pp. 401-408. ISBN 9780081006238, https://doi.org/10.1016/B978-0-08-100623-8.00019-0. (Year: 2018).*

GE Healthcare, 2006 ("Hydrophobic Interaction and Reversed Phase Chromatography Principles and Methods." Handbook 11-0012-69 AA Feb. 2006. Retrieved Dec. 12, 2023 from: https://biocev.lf1.cuni.cz/file/248/hydrophobic-interaction-and-reverse-phase.pdf) (Year: 2006).*

"Increasing productivity in hydrophobic interaction chromatography (HIC) using Capto™ resins" Cytiva Application Note KA7685111119AN, 2020 (Year: 2020).*

Ali-Akbar Golabchifar et al. "Optimization of the simultaneous determination of imatinib and its major metabolite, CGP74588, in human plasma by a rapid HPLC method using D-optimal experimental design" Talanta, vol. 85, Issue 5, 2011, pp. 2320-2329, ISSN 0039-9140,https://doi.org/10.1016/j.talanta.2 (Year: 2011).*

Li et al."Innovative Hydrophobic Interaction Chromatography (HIC) Resins for Next Generation Purification Challenges" Thermo Fisher Scientific, 2017, Retrieved Dec. 27, 2023 from https://assets.thermofisher.com/TFS-Assets/BPD/posters/hic-resins-next-gen-purification-challenges-scientific-poster.pdf (Year: 2017).*

Hall et al. "Use of mobile phase additives for the elution of bispecific and monoclonal antibodies from phenyl based hydrophobic interaction chromatography resins" Journal of Chromatography B, vol. 1096, Oct. 1, 2018, pp. 20-30 (Year: 2018).*

Wang et al "Developing an Anion Exchange Chromatography Assay for Determining Empty and Full Capsid Contents in AAV6.2" Molecular Therapy Methods & Clinical Development vol. 15, p. 257-263 (2019) (Year: 2019).*

Guy-Alain Junter, Laurent Lebrun "Polysaccharide-based chromatographic adsorbents for virus purification and viral clearance" Journal of Pharmaceutical Analysis vol. 10, Issue 4, Aug. 2020, pp. 291-312 (Year: 2020).*

Ghose MAbs. "Purification of monoclonal antibodies by hydrophobic interaction chromatography under no-salt conditions".Sep. 1, 2013; 5(5): 795-800. (Year: 2013).*

Li J.J. et al.: "Monoclonal Antibody Aggregate Polishand Viral Clearance Using HydrophobicInteraction Chromatography," Thermofisher Scientific, vol. 17, No. 11-12, Nov. 2019 (Nov. 2019),-Dec. 2019 (Dec. 2019), pp. 1-7.

Hui F. Liu et al: "Recovery and purification process development for monoclonal antibody production," MABS, vol. 2, No. 5, Sep. 1, 2010 (Sep. 1, 2010), pp. 480-499.

(Continued)

*Primary Examiner* — Janet L Epps-Smith
*Assistant Examiner* — Lea S O'Brien
(74) *Attorney, Agent, or Firm* — Bookoff McAndrews, PLLC

(57) ABSTRACT

The present application provides a method for characterizing and/or determining viral clearance capacity of hydrophobic interaction chromatography (HIC) including experimental design for multivariate analysis of viral clearance of HIC. The method provides understanding of the mechanism of the viral clearance using HIC by running a D-Optimal design of experiment including evaluations of multiple factors, such as pH, buffer concentration, column loading concentration, flow rate of column, or hydrophobic strength of the HIC column.

24 Claims, 25 Drawing Sheets

(56) References Cited

OTHER PUBLICATIONS

International Search Report date of mailing May 4, 2021, International Application No. PCT/US2021/013739, International Filing Date Jan. 15, 2021.
National Institute of Standards and Technology, "5.5.2.1. D-Optimal designs", Engineering Statistics Handbook, 2012, U.S. Department of Commerce, <https://www.itl.nist.gov/div898/handbook/pri/section5/pri521.htm> (last accessed Apr. 4, 2024).

* cited by examiner

|  | Log$_{10}$ adjusted titer (PFU) | 95% Conf. of Log$_{10}$ adjusted titer | Log$_{10}$ reduction | 95% Conf. of Log$_{10}$ reduction |
|---|---|---|---|---|
| Stock virus control | 8.13 | 0.17 | NA | NA |
| HIC load hold control | 3.33 | 0.35 | 4.80 | 0.39 |
| HIC product pool | < 3.47 | NA | > None | 0.35 |

FIG. 12

Bivariate Fit of Infectivity XMuLV LRF By qPCR XmuLV LRF

—— Linear Fit

| Summary of Fit | |
|---|---|
| RSquare | 0.73649 |
| RSquare Adj | 0.732098 |
| Root Mean Square Error | 0.434463 |
| Mean of Response | 2.085161 |
| Observations (or Sum Wgts) | 62 |

HYDROPHOBIC INTERACTION CHROMATOGRAPHY FOR VIRAL CLEARANCE

FIELD

The present invention generally pertains to methods for characterizing viral clearance capacity of hydrophobic interaction chromatography including experimental designs for multivariate analysis.

BACKGROUND

Biological products can be contaminated with unwanted viruses causing a risk of transmitting viral diseases. Global health authorities require evaluation of viral clearance for manufacturing biologics or biotechnology products, since viral load can multiply during the growth of mammalian cell culture. Effective viral clearance studies are an essential part of process validation, which are critical to ensure drug safety. Viral contamination can affect raw materials, cell culture processes, bioreactor and downstream purification processes.

Viral validation studies are designed to provide evidence that the selected operating conditions will effectively inactivate and/or remove viruses. The experimental design of viral clearance studies includes characterization of the manufacturing process to ensure their ability to remove viruses, and improve understanding of processing conditions. When evaluating clearance of viral contaminants, it is justified to select worst-case conditions for evaluation.

The processes of virus inactivation or removal include pH treatment, heat treatment, filtration or chromatography. Chromatography steps can be used to purify biologics products with a potential to provide viral reduction for viral clearance, such as protein A, anion exchange chromatography, or hydrophobic interaction chromatography (HIC). When a chromatography step is used to capture a monoclonal antibody, the virus might interact with the antibody and/or the chromatography resin. For antibody purification using HIC, there is limited understanding of viral clearance related to flow-through mode of HIC, for example, selective binding of unwanted components while the antibody appears in the flow-through.

It will be appreciated that a need exists for methods to effectively characterize the viral clearance capacity of manufacturing processes to ensure drug safety including building a retrospective viral clearance database to explain mechanisms and justify selections of worst-case conditions, such as improving the understanding of the viral clearance capacity of HIC.

SUMMARY

This disclosure provides methods to determine impact of development factors on viral clearance capacity of HIC including experimental design for multivariate analysis of viral clearance of HIC. This disclosure also provides understanding of the mechanism of the viral clearance and understanding of worst-case processing conditions for viral clearance for enhancing drug safety. In addition, this disclosure provides methods to build a retrospective viral clearance HIC database to explain mechanisms and justify selections of worst-case conditions. In order to utilize HIC for viral clearance, this disclosure provides characterization of HIC related to clearance of a model retrovirus to gain understanding of the process.

This disclosure also provides a method of purifying an antibody from a sample comprising one or more impurities including viral particles, the method comprising the steps of: (a) providing the sample comprising the antibody produced in a host-cell, (b) adjusting a pH of the sample to a range of from about 4.2 to about 8.0, (c) loading the sample to a hydrophobic interaction chromatography (HIC) column, wherein a concentration of the sample is from about 40 g/L to about 200 g/L, and (d) collecting the HIC treated sample.

In some exemplary embodiments, citrate buffer is used to adjust the pH of the sample of the method, wherein a concentration of the citrate buffer is from about 10 mM to about 200 mM. In some aspects, a resin of the HIC column of the method is phenyl or capto phenyl resin. In some aspects, a hydrophobic strength of the HIC column of the method is within a range from a weak hydrophobic strength to a strong hydrophobic strength, wherein the weak hydrophobic strength is achieved using a phenyl resin or an equivalent thereof, wherein the strong hydrophobic strength is achieved using a capto phenyl resin or an equivalent thereof.

In some aspects, the antibody of the method is a monoclonal antibody or a bispecific antibody, wherein the antibody has an IgG1 isotype or an IgG4 isotype. In some aspects, a flow rate through the HIC column of the method has a linear velocity of about 100 cm/hr to about 300 cm/hr.

In some aspects, the method of the present application further comprises measuring the presence of viral genomic copies and/or measuring the presence of viral particles. In some aspects, the method of the present application further comprises measuring the presence of both viral genomic copies and viral particles.

This disclosure, at least in part, provides a method of purifying an antibody from a sample comprising one or more impurities including viral particles, the method comprising the steps of: (a) providing the sample comprising the antibody produced in a host-cell, (b) adjusting a pH of the sample to a range of from about 4.2 to about 8.0, (c) loading the sample to a hydrophobic interaction chromatography (HIC) column, wherein a concentration of the sample is from about 40 g/L to about 200 g/L, (d) collecting the HIC treated sample, and (e) measuring the presence of viral genomic copies and/or infectious viral particles in the HIC treated sample of step (d).

In some exemplary embodiments, the method of the present application further comprises optimizing removal of viral genomic copies and/or viral particles by running a D-Optimal design of experiment. In some aspects, the D-Optimal design of experiment of the present application evaluates the following factors: (a) the pH of the sample from about 4.2 to about 8.0, (b) the column loading, wherein a concentration of the sample is from about 40 g/L to about 200 g/L, (c) a linear velocity of a flow rate through the HIC column from about 100 cm/hr to about 300 cm/hr, and (d) a hydrophobic strength of the HIC column from a weak hydrophobic strength to a strong hydrophobic strength; wherein the weak hydrophobic strength is achieved using a phenyl resin or an equivalent thereof, wherein the strong hydrophobic strength is achieved using a capto phenyl resin or an equivalent thereof. In some aspects, the D-Optimal design of experiment of the present application further evaluates an isotype of the antibody, wherein the antibody is a monoclonal antibody or a bispecific antibody.

This disclosure, at least in part, provides a method of purifying an antibody from a sample comprising one or more impurities including viral particles, the method comprising the steps of: (a) providing the sample comprising the antibody produced in a host-cell, (b) adding citrate buffer to the sample, (c) adjusting a pH of the sample to a range of from about 4.2 to about 8.0, (d) loading the sample to a hydrophobic interaction chromatography (HIC) column, wherein a concentration of the sample is is from about 40 g/L to about 200 g/L, (e) collecting the HIC treated sample, and (f) measuring the presence of viral genomic copies and/or viral particles in the HIC treated sample of step (e).

In some exemplary embodiments, the method of the present application further comprises optimizing removal of viral genomic copies and/or viral particles by running a D-Optimal design of experiment, wherein the D-Optimal design of experiment evaluates the following factors: (a) the pH of the sample from about 4.2 to about 8.0, (b) a concentration of the citrate buffer from about 10 mM to about 200 mM, (c) the column loading, wherein a concentration of the sample is from about 40 g/L to about 200 g/L, (d) a linear velocity of a flow rate through the HIC column from about 100 cm/hr to about 300 cm/hr, and (e) a hydrophobic strength of the HIC column from a weak hydrophobic strength to a strong hydrophobic strength, wherein the weak hydrophobic strength is achieved using a phenyl resin or an equivalent thereof, wherein the strong hydrophobic strength is achieved using a capto phenyl resin or an equivalent thereof. In some aspects, the antibody of the method is a monoclonal antibody or a bispecific antibody.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

FIG. 12 shows data analysis obtained from DoE studies using bivariate fit of infectivity X-MuLV LRF by qPCR X-MuLV LRF to support relationship between LRF by infectivity and qPCR assays according to an exemplary embodiment.

DETAILED DESCRIPTION

Figure 1:
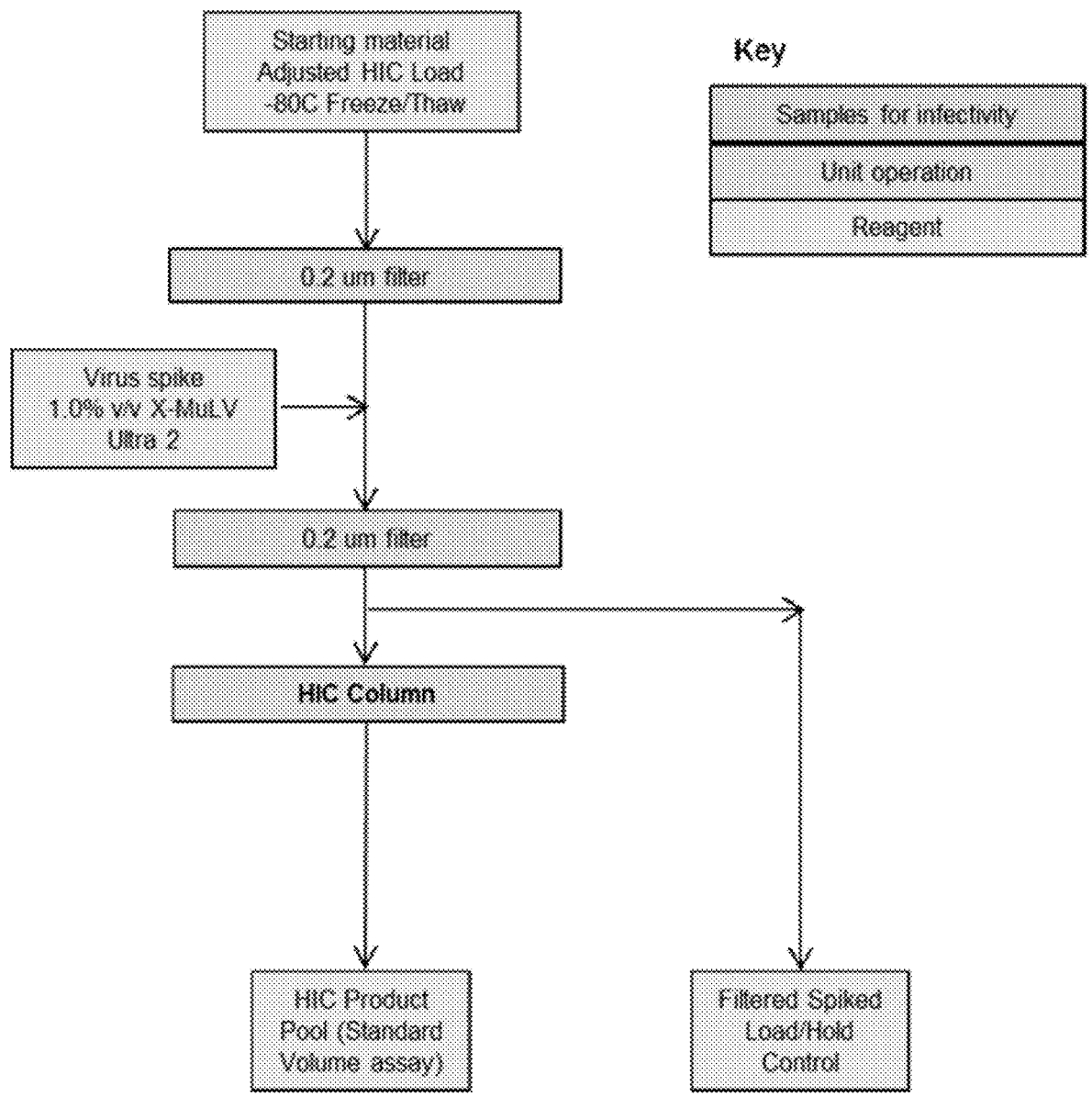
FIG. 1 shows overview of an exemplary process for viral clearance quantitation using virus assays according to an exemplary embodiment.

Since viral contaminations can multiply during the growth of mammalian cell culture, evaluation of viral clearance for manufacturing biologics or biotechnology products is essential and critical to ensure drug safety. Health authorities have provided guidance that amounts to "Use Good Science" to manage patient risk for evaluating whether a step clears virus—by knowing how clearance happens, when steps operate independently of each other, whether their capability is additive or not additive, and knowing what affects performance. The evaluation of viral clearance should include demonstrating removal of a specific model virus for retrovirus-like particles which are inherent in the genome of Chinese hamster ovary (CHO) cells (Anderson et al., Endogenous origin of defective retroviruslike particles from a recombinant Chinese hamster ovary cell line, Virology 181 (1): 305-311, 1991). Xenotropic murine leukemia virus (X-MuLV) can be used as a model virus in the evaluation of viral inactivation in CHO cell-derived pharmaceutical proteins. Murine Leukemia virus (MuLV) is a retrovirus and has a positive single-stranded sense RNA that replicates via reverse transcription. MuLV can induce leukemia in inoculate mice.

It is important to ensure viral clearance when designing a purification process. Typical workflow for studying viral clearance of a manufacturing process includes spiking the sample load with virus, running the process on a scale-down experiment to mimic a large-scale step and documenting the ability to clear the spiked virus. Regulatory guidelines recommend using virus validation data to design in-process limits for determining critical process parameters, such as conducting validations at process extremes. Tests can be performed under worst-case conditions to demonstrate the minimum clearance which a process step can provide (1998, Q5A Viral Safety Evaluation of Biotechnology Products Derived from Cell Lines of Human or Animal Origin. T. I. C. f H. o. T. R. f P. f H. Use). Worst-case conditions can be determined by factors that influence the viral clearance mechanism depending on the process used. The worst-case conditions can be tested to demonstrate the minimal viral reduction of a specific process step (Aranha et al., Viral clearance strategies for biopharmaceutical safety, part II: a multifaceted approach to process validation, BioPharm 14 (5), 43-54, 90, 2001).

Viral validation studies can be designed to document the selected operating conditions regarding product quality and process specificity to assure viral safety. The processes of virus inactivation or removal include pH treatment, heat treatment, solvent/detergent treatment, filtration or chromatography. Low pH incubation can be used to inactive enveloped virus, such as irreversible denaturation of capsid (Brorson et al., Bracketed generic inactivation of rodent retroviruses by low pH treatment for monoclonal antibodies and recombinant proteins, Biotechnol Bioeng 82(3): 321-329, 2003). Filtration is a size-based removal which can be used to remove both enveloped and non-enveloped viruses (Lute et al., Phage passage after extended processing in small-virus-retentive filters, Biotechnol Appl Biochem 47(Pt 3): 141-151, 2007). Chromatography steps can be used to purify biologics products with a potential to provide viral reduction for viral clearance, such as protein A (Bach et al., Clearance of the rodent retrovirus, XMuLV, by protein A chromatography, Biotechnol Bioeng 112(4): 743750, 2015) or anion exchange chromatography (Strauss et al., Anion exchange chromatography provides a robust, predictable process to ensure viral safety of biotechnology products, Biotechnol Bioeng 102(1): 168-175, 2009a).

Some of the chromatography steps can contribute to virus clearance, such as using anion exchange or hydrophobic interaction chromatography (HIC) for log reductions in the order of 4 to 5 logs (Brown et al., A step-wise approach to define binding mechanisms of surrogate viral particles to multi-modal anion exchange resin in a single solute system. Biotechnol. Bioeng., 114(7), p. 1487-1494, 2017). Multimodal anion exchange resins often display a high and robust viral clearance in a very broad pH and conductivity window. Cation exchange and protein A affinity also contribute to viral reduction in the order of 2 to 3 logs (Ruppach, $Log_{10}$ Reduction Factors in Viral Clearance Studies, BioProcess. J., 12(4), 24-30 https://www.bioprocessingjournal.com/, online posting date Jan. 7, 2014). Several critical variables in chromatographic processes can affect viral clearance, including sample loading concentrations (such as antibody loading), contaminant concentrations, buffers, pH, flow rates, wash volumes and temperatures, depending on the resin and binding mode. Changing these conditions can provide indications of the viral reduction capabilities of the process.

The requirements for evaluating viral clearance for manufacturing biologics or biotechnology products by the global health authority have led to an increasing demand for characterizing the viral clearance capacity of the manufacturing process. This disclosure provides experimental design for multivariate analysis of viral clearance of HIC to satisfy the aforementioned demand, which can provide understanding of the mechanism of the viral clearance for enhancing drug safety.

This disclosure provides methods to characterize viral clearance capacities of HIC to evaluate and validate HIC by identifying the impacts of development factors including experimental design for multivariate analysis. The experimental design, for example, design of experiments, or DoE, for multivariate analysis includes critical characterizations of the HIC process by identifying significant development factors to improve understanding of processing conditions for maximizing viral clearance. This disclosure provides a capacity to build a retrospective viral clearance HIC database to explain mechanism and justify selection of worst-case conditions.

DoE is a methodology which allows systematic variations of multiple development factors within the context of one experimental design. The results of DoE can be used to create mathematical models of the process being examined. The true optimum of the examined process can be identified by applying these mathematical models. Applications of DoE results include eliminating insubstantial development factors, identifying critical development factors for further study and predicting the performance of examined process. DoE is conducted in a systematic logical flow including stating objectives, selecting variable factors and models, creating experimental designs to support the models, collecting data based on the designs, executing the analysis, verifying the models with check points and reporting the outcomes.

Typical workflow for studying viral clearance of a chromatography step includes spiking the sample load with virus, running the chromatography step on a scale-down column, and documenting the ability to clear the spiked virus. Viral clearance studies are usually performed using a scale-down model by using a small-scale chromatography column to mimic a large-scale step with same bed height and flow velocity. DoE can facilitate the determination of worst-case conditions to identify development factors that influence the viral clearance mechanism depending on the process used. Then, the worst-case conditions can be tested to demonstrate the minimal viral reduction of a specific process step.

For antibody purification, there is limited understanding of viral clearance related to negative mode (flow-through mode) of HIC, for example, selective binding of unwanted components while the antibody appears in the flow-through. A limitation of HIC is that high salt concentrations are necessary for protein binding in considering protein aggregation. In order to utilize HIC for viral clearance, this disclosure provides characterization of HIC related to clearance of a model retrovirus to gain understanding of the process. The impact of development factors regarding the viral clearance capacity of HIC can be determined to improve understanding of worst-case processing conditions for viral clearance toward the path to maximizing clearance.

Viral clearance studies are measurements of the capacity of the dedicated manufacturing process steps to inactivate or remove viruses. Model viruses can be spiked into a specific process and then experiments can be conducted to demonstrate the inactivation or removal of spiked viruses during subsequent processing steps. Virus loads of the spiked process intermediate and product-relevant process samples can be determined for estimation of the reduction factors. Methods for virus quantitation of the present application include virus specific cell based infectivity assays and quantitative polymerase chain reaction (qPCR). Viruses comprise DNA or RNA encapsulated by a protein coat with or without envelopes.

Viral reduction refers to the difference between the total virus amounts in the input sample and output sample after performing the specific process step, such as the chromatography process. The viral reduction capability can be defined as the logarithmic reduction value (LRV) or logarithmic reduction factor (LRF) of a process step. The reduction factor is calculated based on the total virus load before applying the clearance step and the total virus amount after applying the clearance step. Viral validation studies can be conducted to document clearance of known viruses associated with the product and to estimate the effectiveness of the process to clear potential adventitious viral contaminants by characterizing the ability of the process to clear non-specific model viruses.

Evaluation and validation of a process regarding viral reduction include a critical analysis of the process to determine potential pathogenic sources of viral contaminations or to characterize the process to identify which steps in the manufacturing process have the potential for conducting viral clearance. Each process step to be examined can be evaluated for the viral clearance mechanism, such as by inactivation, removal or a combination thereof. It is preferable to select an effective and robust step which can remove viral contaminations independent of variable process parameters. (Aranha et al.).

This disclosure also provides methods to determine impact of development factors on viral clearance capacity of HIC by identifying multiple significant development factors including pH of the buffer, sodium citrate concentration in the buffer, sample loading, linear velocity of flow rate, hydrophobic strength of HIC resin, and isotype of monoclonal antibody. This disclosure also provides understanding of worst-case processing conditions for viral clearance. The development factors in overall worst-case HIC clearance include high pH, low-medium citrate buffer concentration, high column loading, fast linear velocity, IgG4 monoclonal antibody isotype and a phenyl Sepharose 6 FF HS (weak HIC resin). The results of DoE and resultant models can be used to confirm, reject, or alter existing understanding of HIC mechanism for viral clearance.

Exemplary embodiments disclosed herein satisfy the aforementioned demands by providing methods and systems for characterizing viral clearance capacity of HIC including experimental design for multivariate analysis to identify the impact of development factors.

In some exemplary embodiments, methods are provided for purifying an antibody from a sample comprising one or more impurities including viral particles. Removal of viral particles and/or viral genomic copies are evaluated using HIC for viral clearance.

The term "a" should be understood to mean "at least one"; and the terms "about" and "approximately" should be understood to permit standard variation as would be understood by those of ordinary skill in the art; and where ranges are provided, endpoints are included.

As used herein, the terms "include," "includes," and "including," are meant to be non-limiting and are understood to mean "comprise," "comprises," and "comprising," respectively.

In some exemplary embodiments, this disclosure provides a method of purifying an antibody from a sample comprising one or more impurities including viral particles, the method comprising the steps of: (a) providing the sample comprising the antibody produced in a host-cell, (b) adjusting a pH of the sample to a range of from about 4.2 to about 8.0, and (c) loading the sample to a hydrophobic interaction chromatography (HIC) column, wherein a concentration of the sample is from about 40 g/L to about 200 g/L, and (d) collecting the HIC treated sample of step (c).

As used herein, the term "antibody" refers to immunoglobulin molecules consisting of four polypeptide chains, two heavy (H) chains and two light (L) chains inter-connected by disulfide bonds. Each heavy chain has a heavy chain variable region (HCVR or $V_H$) and a heavy chain constant region. The heavy chain constant region contains three domains, $C_H1$, $C_H2$ and $C_H3$. Each light chain has of a light chain variable region and a light chain constant region. The light chain constant region consists of one domain ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ can be composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" is inclusive of, but not limited to, those that are prepared, expressed, created or isolated by recombinant means, such as antibodies or bispecific antibodies isolated from a host cell transfected to express the antibody. An IgG comprises a subset of antibodies.

As used herein, the term "impurity" can include any undesirable protein present in the protein biopharmaceutical product. Impurity can include process and product-related impurities. The impurity can further be of known structure, partially characterized, or unidentified. Process-related impurities can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables. Product-related impurities (e.g., precursors, certain degradation products) can be molecular variants arising during manufacture and/or storage that do not have properties comparable to those of the desired product with respect to activity, efficacy, and safety. Such variants may need considerable effort in isolation and characterization in order to identify the type of modification(s). Product-related impurities can include truncated forms, modified forms, and aggregates. Truncated forms are formed by hydrolytic enzymes or chemicals which catalyze the cleavage of peptide bonds. Modified forms include, but are not limited to, deamidated, isomerized, mismatched S—S linked, oxidized, or altered conjugated forms (e.g., glycosylation, phosphorylation). Modified forms can also include any post-translational modification form. Aggregates include dimers and higher multiples of the desired product. (Q6B Specifications: Test Procedures and Acceptance Criteria for Biotechnological/Biological Products, ICH August 1999, U.S. Dept. of Health and Humans Services).

In some exemplary embodiments, the method of the present application further comprises optimizing removal of viral genomic copies and/or viral particles by running a D-Optimal design of experiment, wherein the D-Optimal design of experiment of the present application evaluates the following factors: (a) the pH of the sample from about 4.2 to about 8.0, (b) the column loading, wherein a concentration of the sample is from about 40 g/L to about 200 g/L, (c) a linear velocity of a flow rate through the HIC column from about 100 cm/hr to about 300 cm/hr, (d) a hydrophobic strength of the HIC column from a weak hydrophobic strength to a strong hydrophobic strength, and (e) an isotype of the antibody.

As used herein, the term "isotype" refers to different isotypes of immunoglobulines. Immunoglobulins are heterodimeric proteins composed of two heavy and two light chains. Immunoglobulin has variable domains that binds antigens and constant domains that specify effector functions. The Fc portion of the heavy chains defines the class of antibody, of which there are five in mammalians: IgG, IgA, IgM, IgD and IgE. The classes differ in their biological properties, otherwise known as effector functions, and their functional localization to ensure an appropriate immune response for a given antigen. There are five main classes of heavy chain constant domains. Each class defines the isotypes of IgM, IgG, IgA, IgD, and IgE. IgG can be categorized into four subclasses, for example, IgG1, IgG2, IgG3, and IgG4. IgA can be categorized into IgA1 and IgA2. When the antibody can be a human antibody, an isotype of the human antibody can be IgG1, IgG2, IgG3, IgG4, IgA1, IgA2, IgM, or IgE. When the antibody is a monkey antibody, an isotype of the monkey antibody can be IgG1, IgG2, IgG3, IgG4, IgM, or IgA.

Exemplary Embodiments

Embodiments disclosed herein provide methods for purifying an antibody from a sample comprising one or more impurities including viral particles. The method includes optimizing removal of viral genomic copies and/or viral particles by running a D-Optimal design of experiment.

In some exemplary embodiments, this disclosure provides a method of purifying an antibody from a sample comprising one or more impurities including viral particles, the method comprising the steps of: (a) providing the sample comprising the antibody produced in a host-cell, (b) adjusting a pH of the sample to a range of from about 4.2 to about 8.0, (c) loading the sample to a HIC column, wherein a concentration of the sample is from about 40 g/L to about 200 g/L, and (d) collecting the HIC treated sample of step (c).

In some aspects, a resin of the HIC column of the method is phenyl Sepharose 6 FF HS resin or capto phenyl HS resin. In some aspects, a hydrophobic strength of the HIC column of the method is within a range of from a weak hydrophobic strength to a strong hydrophobic strength, wherein the weak hydrophobic strength is achieved using a phenyl Sepharose 6 FF HS resin or an equivalent thereof, wherein the strong hydrophobic strength is achieved using a capto phenyl HS resin or an equivalent thereof. In some aspects, the HIC resin comprises a hydrophobic group which is phenyl, capto phenyl, octyl, butyl, hexyl or propyl.

It is understood that the method or system is not limited to any of the aforesaid hydrophobic interaction chromatography or processing conditions thereof. The consecutive labeling of method steps as provided herein with numbers and/or letters is not meant to limit the method or any embodiments thereof to the particular indicated order. Various publications, including patents, patent applications, published patent applications, accession numbers, technical articles and scholarly articles are cited throughout the specification. Each of these cited references is incorporated by reference, in its entirety and for all purposes, herein. Unless described otherwise, all technical and scientific terms used herein have the same meaning as commonly understood by one of ordinary skill in the art to which this invention belongs.

The disclosure will be more fully understood by reference to the following Examples, which are provided to describe the disclosure in greater detail. They are intended to illustrate and should not be construed as limiting the scope of the disclosure.

EXAMPLES

Methods for Designs of Experiments
1.1 Selecting Development Factors

Various development factors (parameters) for design of experiments (DoE) of HIC were selected to investigate the impacts of development factors toward the viral clearance capacity of HIC to improve understanding of processing conditions for maximizing viral clearance. The development factors with theoretical impacts to the viral clearance of HIC were selected. The development factors which were routinely studied for phase designs relevant to low level risk assessment (LLRA) were also selected. Development factors were evaluated to broaden the understanding of the viral clearance mechanism for communicating with regulatory agencies, such as the isotypes of monoclonal antibodies or hydrophobic strength of HIC resin. The selected development factors and their retrovirus safety risk ranking are listed in Table 1 including concentration of the sample loaded onto the column (g/L), pH of the buffer, linear velocity of the flow rate (cm/hr), loading of host cell protein (HCP in ppm), loading of high molecular weight (HMW) dimer protein (%), loading of high molecular weight (HMW) protein with higher order (%), concentration of sodium citrate (mM), cycled number of the HIC resin, concentration of protein loading, and operating temperature (Celsius). Other development factors which were not selected in the studies were assessed by residual analysis of pre-existing experimental data.

The results indicate that operating temperature factors are expected to have limited impacts on phase design. The control of operating temperature factors was difficult to be implemented in the virus laboratory (Lu et al., Recent Advancement in Application of Hydrophobic Interaction Chromatography for Aggregate Removal in Industrial Purification Process, Current Pharmaceutical Biotechnology, 2009, 10, 427-433). Cycled (reused) HIC resin showed no impacts on viral clearance studies. Load impurity factors were difficult to measure (offsite study) and control.

TABLE 1

Selected development factors

| Factors (X) | Retrovirus Safety Risk Ranking |
|---|---|
| Loading (g/L) | 9 |
| pH | 6 |
| Linear velocity (cm/hr) | 6 |
| Load HCP (ppm) | 6 |
| Load HMW, dimer (%) | 3 |
| Load HMW, higher order (%) | 3 |
| Sodium citrate concentration (mM) | 3 |
| Cycled number | 3 |
| Load concentration | 3 |
| Operating temperature (Celsius) | 3 |

2.1 Selecting Development Factors for Experimental Designs for Viral Clearance of HIC Various ranges of the development factors were selected for design of experiments (DoE) for viral clearance (VC) of HIC. In order to maximize signal-to-noise ratio, wide ranges of development factors were selected as shown in Table 2 including ranges for pH, citrate concentration, column loading, linear velocity, hydrophobic strength (HIC resin), and isotypes of monoclonal antibodies. The rationale for selecting the range of pH 4.2-8.0 is that low pH has shown improvement of host cell protein clearance for some programs. In particular, pH 4.2 was selected as the lower limit of pH which was expected to have no impact on product quality. The rationale for selecting the range of citrate at 10-200 mM is to select broad range of citrate concentration, since kosmotrope strength may modulate virus adsorption to the column. The rationale for selecting the range of column loading at 40-200 g/L is that higher column load may represent worst-case for viral clearance due to competitive binding. The rationale for selecting linear velocity at 100-300 cm/hr is that the variations of contact time may limit virus adsorption. In particular, it is expected that shorter contact time may decrease diffusion which could limit virus adsorption. IgG1 and IgG4 isotypes were selected to include load attribute to satisfy potential regulatory requirements.

TABLE 2

Range selections of development factors for DoE for viral clearance of HIC

| Factors | VC DoE Ranges | Phase design references | Ranges in pre-existing experimental data |
|---|---|---|---|
| pH | 4.2-8.0 | Common HIC multivariate DoE range is 4.5-6.0. | 4.4-8.0 |
| Citrate | 10-200 mM | Common HIC multivariate DoE range is 10-50 mM. | 20-150 |
| Column loading | 40-200 g/L | Common HIC multivariate DoE range is 50-150 g/L | 80-160 |
| Linear velocity | 100-300 cm/hr | HIC multivariate DoE range | 150-200 |
| Hydrophobic strength (HIC resin) | Weak (phenyl Sepharose 6 FF HS); strong (capto phenyl HS) | 10 resins evaluated by high throughput screening | Only capto phenyl |
| mAb isotype | IgG1, IgG4 | IgG1/IgG4 | Primarily IgG4 |

The ranges of the development factors were further verified to ensure that wide factor ranges do not result in impossible factor combinations, since the operations under such wide factor ranges may have the risk of failure in HIC runs possibly due to irreversible binding or elevated column pressure. Pre-study experiments were conducted to confirm design space at worst-case HIC performance, such as yield % and cleaning strategy. The pre-study experiments include: screening runs at low pH 4.2, low loading at 40 g/L concentration, high citrate concentration at 200 mM for each monoclonal antibody (mAb) on each resin; estimating area under the curve analysis (AUC) to verify the column cleaning effects using 6N guanidine HCl; and assessing the impacts of freeze/thaw process on the load material. The pre-study runs do not show significant failure modes as shown in Table 3.

TABLE 3

Pre-study experiments

| mAb | Resin | Yield (%) | HMW % Clearance Factor | AUC post guanidine (% of total) |
|---|---|---|---|---|
| mAb14 | Capto phenyl HS | 57.0 | 19 | 0.01 |
| mAb14 | Phenyl Sepharose 6 FF HS | 87.0 | 5.6 | 0.05 |
| mAb11 | Capto phenyl HS | 28.0 | 16 | 0.09 |
| mAb11 | Phenyl Sepharose 6 FF HS | 72.0 | 3.3 | 0.01 |

Since some uncontrolled variables may be present, certain conditions were monitored, such as monitoring a number of column runs, processing temperature (such as room temperature), virus lot consistency or AKTA system (a preparative chromatography system for method and process development), by capturing the uncontrolled variables in residuals or RMSE (square root of the variance of the residuals). Different variable load concentrations were used for different load pH or different citrate concentrations (mM) to enable column loading shown in Table 2. For the validation of viral clearance assays, preliminary testing was performed on only worst-case conditions, such as low pH or high citrate concentrations. In addition, preliminary testing dilution for worst-case conditions were applied to all runs.

3.1 Overview of the Process

The quantitation of viruses was conducted using two virus assays, e.g., infectivity and qPCR (Xu et al., An overview of quantitative PCR assays for biologicals: quality and safety evaluation, Dev Biol (Basel) 113: 89-98, 2003). The infectivity assay is a cell-based assay relevant to specific virus which is conducted by measuring infectious virus particles. Lack of infectivity denotes either viral inactivation or virus removal. The infectivity assays are relevant to patient safety, since they represent virus that could potentially infect a patient. The quantitation using qPCR only detected the presence of viral genomic copies. Lack of genomic copies denotes virus removal. In order to maximize the number of runs, sampling plans were limited. The use of assays with standard volume can limit assay sensitivity, however, the LRF ranges at 0-4 were achievable.

The overview of the exemplary process is illustrated in FIG. 1. The starting material, for example, adjusted HIC load with −80° C. freeze/thaw, was subjected to filtration using 0.2 μm filter. Subsequently, model virus, for example, X-MuLV at 1.0% v/v, was spiked to the material followed by filtration using 0.2 μm filter. Subsequently, the spiked and filtered material was subjected to a HIC column to obtain HIC product pool which were then subjected to standard volume assay. Some of the spiked and filtered material was retained as hold control.

Figure 2:
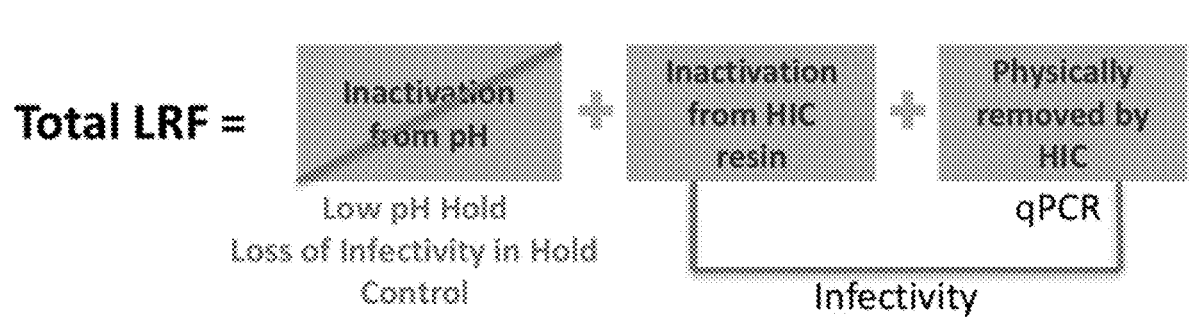
FIG. 2 shows calculation of total logarithmic reduction factor (LRF) for viral clearance quantitation according to an exemplary embodiment.

Total LRF can be calculated by combining the results from inactivation from pH, inactivation from HIC resin and physical removal by HIC. The LRFs contributed by inactivation from HIC resin and physical removal by HIC can be quantitated using infectivity assays. The LRF contributed by physical removal by HIC can also be quantitated using qPCR. Regarding the LRF contributed by inactivation from pH, loss of infectivity can be obtained in hold control due to low pH holds as shown in FIG. 2.

The method of HIC includes the use of a three column volume for equilibration, the use of a six column volume step for washing and the use of a 6 M guanidine HCl to strip the column after each cycle. Examples of DoE method for viral clearance of HIC are shown in Table 4.

TABLE 4

DoE methods for viral clearance of HIC

| Step Name | Solution | Column Volume | Linear Velocity (cm/hr) | Flow Direction |
|---|---|---|---|---|
| Pre-strip | Purified water | 2 | 200 | Down flow |
| Equilibration | N/A | 3 | 200 | Down flow |
| Loading | N/A | N/A | N/A | Down flow |
| Wash | N/A | 6 | N/A | Down flow |
| Strip 1 | 6N guanidine-HCl | 4 | 200 | Up flow |
| Strip 2 | Purified water | 2 | 200 | Up flow |
| Strip 3 | 1N NaOH | 2 | 200 | Down flow |
| Column storage | 0.1N NaOH | 2 | 200 | Down flow |

4.1 D-Optimal Design to Evaluate Factor Ranges

Figure 3:
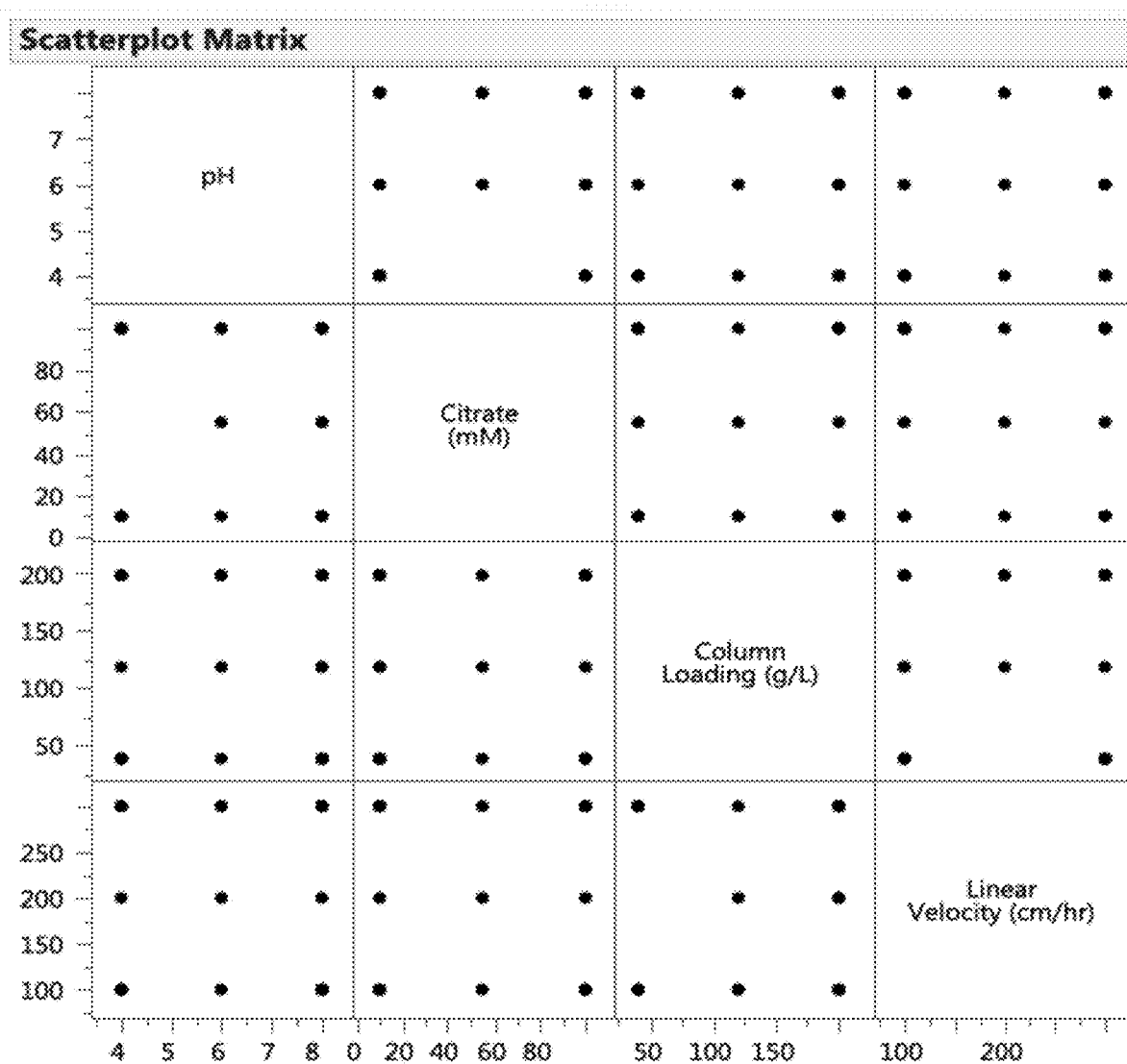
FIG. 3 shows Scatterplot matrix for D-optimal designs which were used to elucidate main effects, interactions and quadratics to evaluate wide ranges of development factors including pH, citrate, column loading, linear velocity or HIC resin according to an exemplary embodiment.

D-optimal designs were used to elucidate main effects, interactions and quadratics as shown in FIG. 3. Twenty-eight runs of D-optimal DoE were used to evaluate wide ranges of development factors including: pH at 4.2, 6.1, or 8.0; citrate buffer concentration at 10 mM, 105 mM or 200 mM; column loading concentration at 40 g/L, 120 g/L or 200 g/L; linear velocity at 100 cm/hr or 300 cm/hr; HIC resin with phenyl Sepharose 6 FF (weak) or capto phenyl HS (strong); or monoclonal antibody of IgG1 or IgG4.

D-optimal designs were generated by computer algorithms to correlate estimated effects. Optimizations of D-optimal designs were generated based on chosen optimality criterions and the fitted models. The optimality of a given D-optimal design was model dependent. The computer algorithm chose the optimal set of design runs from a candidate set of possible design treatment runs according to requested total number of treatment runs for an experiment and a specified model. The candidate set was a collection of treatment combinations from which the D-optimal algorithm chose the treatment combinations to include in the design. The candidate set of treatment runs comprised possible combinations of various factor levels to be incorporated to the experiment.

Three responses were obtained including X-MuLV LRF by infectivity (physical removal and inactivation), X-MuLV LRF by qPCR (physical removal only) and step yield (%). All interactions and quadratics were included in the designs.

Example 1. Low pH for Viral Inactivation for Characterizing Multivariate Analysis of DoE Twenty-eight runs of D-optimal DoE were used to evaluate wide ranges of development factors including pH at 4.2, 6.1, or 8.0. qPCR data served as representative measurements for residual virus at low pH conditions, since previous studies have shown that reverse transcriptase quantitative real-time polymerase chain reaction (qRT-PCR) can be used to replace infectivity assay when the mechanism of virus clearance is physical removal. A previous study shows that infectivity assay and qRT-PCR were closely correlated ($r=0.85$, $P<0.05$, $n=22$) (Anwaruzzaman et al., Evaluation of infectivity and reverse transcriptase real-time polymerase chain reaction assays for detection of xenotropic murine leukemia virus used in virus clearance validation, Biologicals 43: 256-265, 2015).

Figure 4:
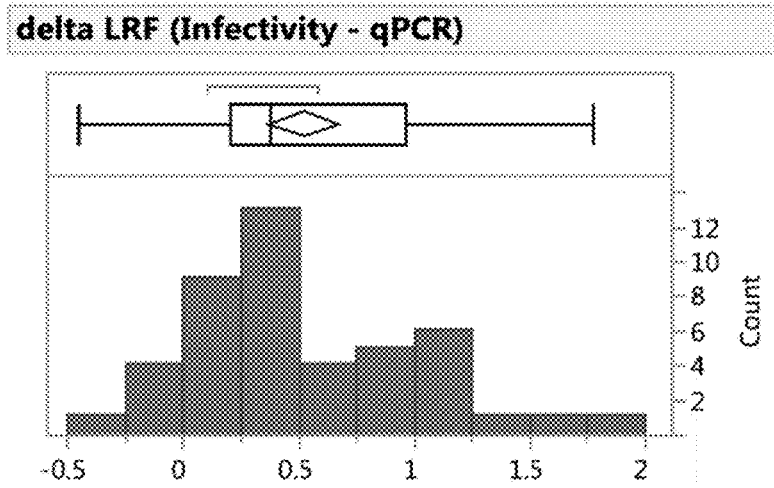
FIG. 4 shows virus quantitation for stock virus control, HIC load hold control and HIC product pool according to an exemplary embodiment.

Eleven runs of the twenty-eight runs with low pH at 4.2 had complete inactivation of viral load infectivity which was independent of other load properties. Virus quantitation was conducted for stock virus control, HIC load hold control and HIC product pool as shown in FIG. 4. The mean difference between infectivity and qPCR within the retrospective dataset is 0.5 LRF which is within accepted assay variability.

Based on the experimental results, two distinct models for viral clearance of HIC DoE were generated: a reported LRF model and qPCR LRF model. The reported LRF model was generated from the combination of LRFs determined by infectivity and qPCR assays. The reported LRF model included qPCR data for low pH runs, since it is inappropriate to use the infectivity assay based on observed chemical inactivation unrelated to HIC. The reported LRF model used infectivity LRF for pH 6.1 and pH 8.0 runs. The qPCR LRF model was generated from solely LRFs obtained by qPCR data which measures the presence of viral genomic copies (physical removal). Both models demonstrate orthogonal clearance to other unit operations for viral inactivation, such as dedicated low pH hold at approximately pH 3.60. qPCR LRF model is less variable compared to reported LRF model due to single clearance mechanism for qPCR.

Figure 5:
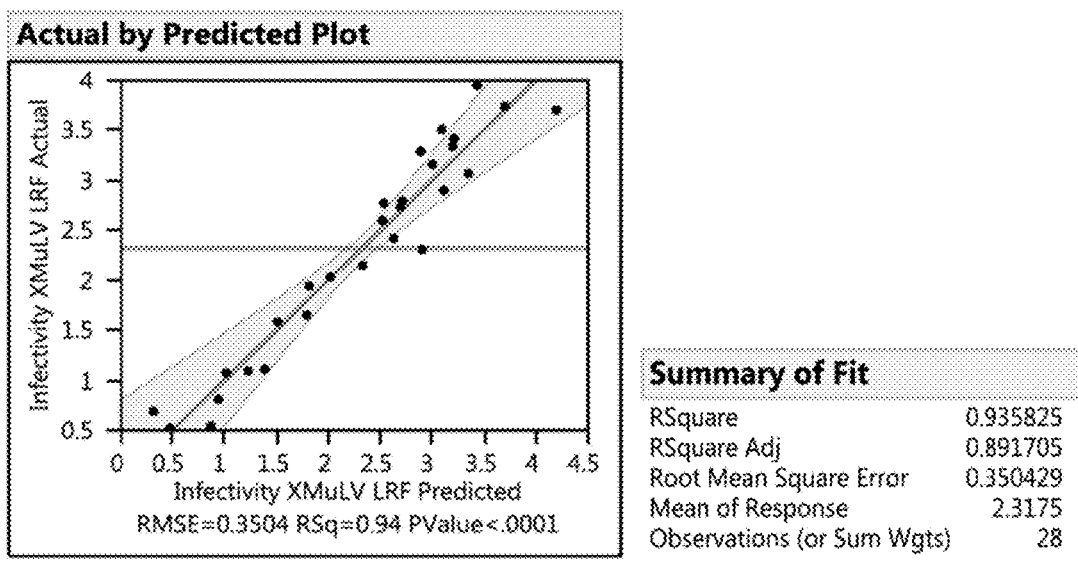
FIG. 5 shows a predicted plot which was generated based on actual Reported LRF and predicted Reported LRF to evaluate viral clearance of X-MuLV according to an exemplary embodiments.

Example 2. Identification of Significant Development Factors Using Reported LRF Model Viral clearance of X-MuLV was evaluated by generating a predicted plot based on actual reported LRF and predicted reported LRF as shown in FIG. 5. Reported LRF model was used to identify multiple significant development factors as shown in FIG. 5. All variance inflation factors (VIF) were about 1 without removing any outliers. When qPCR data was omitted, it resulted in a poor model fit due to low signal-noise ratio. Even though some scaled estimates were statistically significant, they may not be considered as practically significant when applied to each monoclonal antibody program in the context of standard process parameter tolerance. In addition, the effect of specific isotype of monoclonal antibody cannot be perceived.

Figure 6:
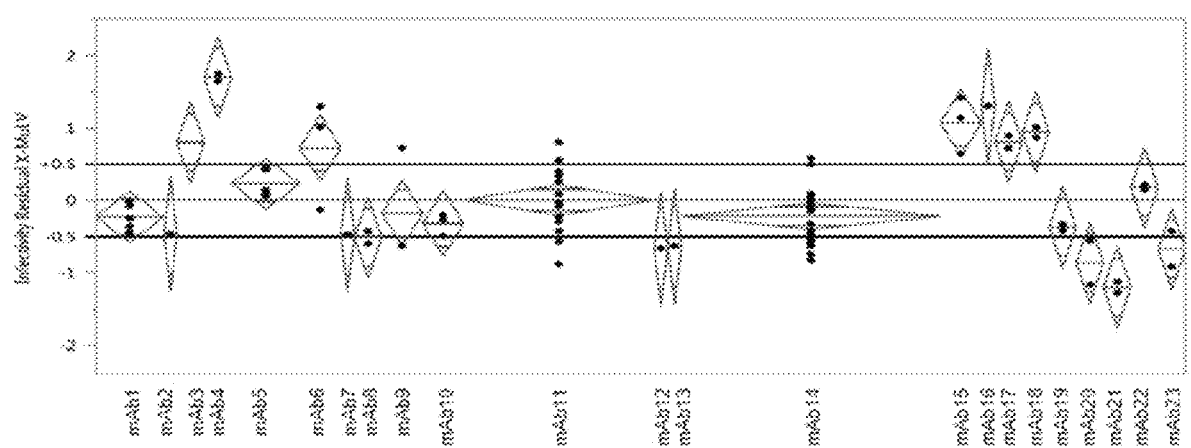
FIG. 6 shows one-way analysis of infectivity of residual X-MuLV by program by applying a reported clearance model to a retrospective dataset to predict the behavior of specific monoclonal antibodies according to an exemplary embodiment. Twenty-three monoclonal antibodies were tested using one-way analysis of infectivity residual X-MuLV by program according to an exemplary embodiment.

Example 3. Predictability by Applying Reported Clearance Model for Monoclonal Antibodies A reported clearance model was used to predict the behavior of specific monoclonal antibodies. When the reported clearance model was applied to a retrospective dataset, the results show adequate prediction for the behavior of specific monoclonal antibodies as shown in FIG. 6. Twenty-three monoclonal antibodies were tested using one-way analysis of infectivity residual (i.e., actual-predicted) X-MuLV by program. Nineteen monoclonal antibodies within twenty-three tested monoclonal antibodies show 95% CI (confidence intervals) of mean residual LRF which is within 0.5 LRF of zero (where actual=predicted). The LRF of mAb4 was outside of 0.5 LRF. mAb4 had lowest pI in dataset at 6.2 with the highest non-DoE citrate buffer concentration of 150 mM.

Figure 7:
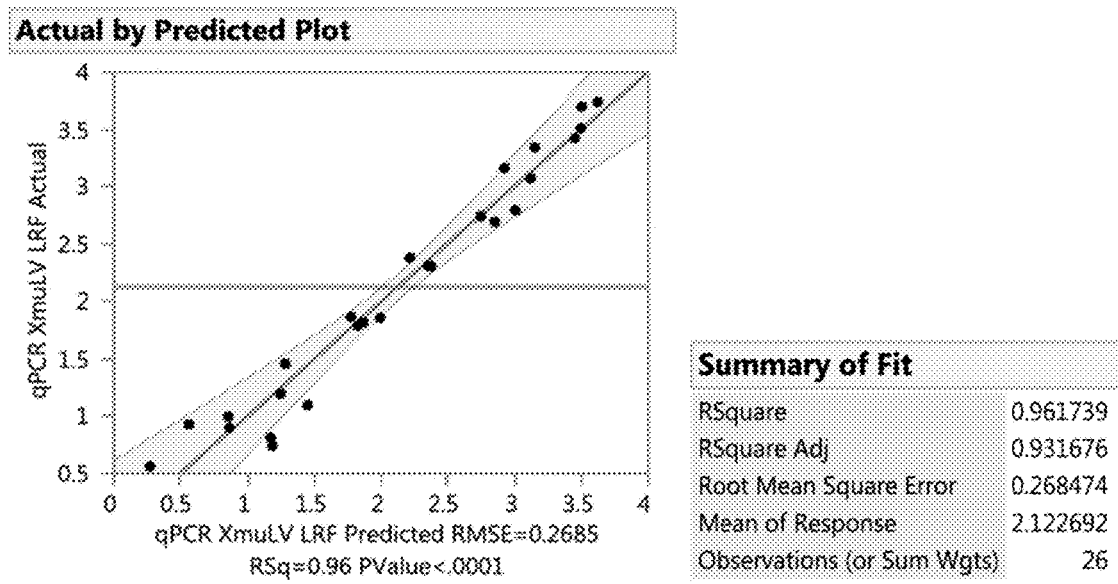
FIG. 7 shows the evaluation of viral clearance of X-MuLV by generating a predicted plot based on actual qPCR LRF and predicted qPCR LRF according to an exemplary embodiment. A qPCR LRF model was used to identify multiple significant development factors according to an exemplary embodiment.

Example 4. Identification of Significant Development Factors Using qPCR LRF Model Viral clearance of X-MuLV was evaluated by generating a predicted plot based on actual qPCR LRF and predicted qPCR LRF as shown in FIG. 7. qPCR LRF model was used to identify multiple significant development factors as shown in FIG. 7. The results show differences compared to reported LRF model. All variance inflation factors (VIF) were about 1 with removal of two outliers. The results show higher R-square with lower RMSE compared to reported LRF model due to measurement of a single viral clearance mechanism by qPCR. The results obtained from qPCR LRF model indicate larger impact of pH compared to reported LRF model. The results indicate that the development factor of citrate may not be significant for virus removal.

Figure 8:
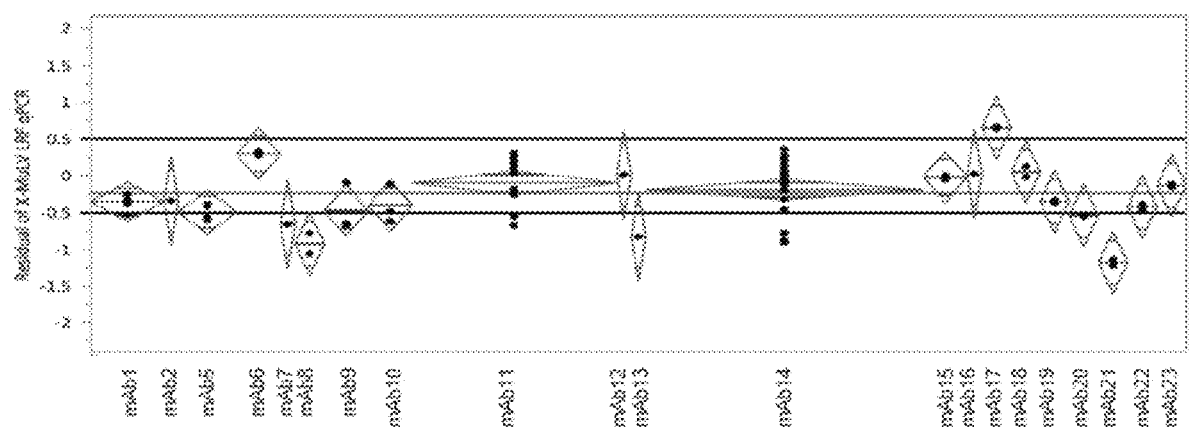
FIG. 8 shows one-way analysis of residual qPCR by program by applying a qPCR model to predict the behavior of specific monoclonal antibodies according to an exemplary embodiment. Twenty-one monoclonal antibodies were tested using one-way analysis of residual GenReg qPCR by program according to an exemplary embodiment.

Example 5. Predictability by Applying qPCR Model for Monoclonal Antibodies qPCR model was used to predict the behavior of specific monoclonal antibodies. When qPCR model was applied to retrospective dataset, the results show adequate prediction for the behavior of specific monoclonal antibodies as shown in FIG. 8. Twenty-one monoclonal antibodies were tested using one-way analysis of residual LRF (i.e., actual-predicted) by program. Twenty monoclonal antibodies within twenty-one tested monoclonal antibodies show 95% CI (confidence intervals) of mean residual LRF which is within 0.5 LRF of prediction without the presence of qPCR data of mAb4. The results indicate lower variation between runs compared to reported LRF (mostly infectivity).

The DoE dataset was compared to the retrospective database to gain understanding of viral clearance of HIC as shown in Table 5. The retrospective dataset has higher number of specific monoclonal antibodies with limited process variance. The DoE dataset has a lesser number of specific monoclonal antibodies with a wider ranges of process variances. When DoE models were applied to only viral clearance studies with less than 1 LRF, the results lead to more understanding of the viral clearance of HIC as shown in Table 6. mAb indicates monoclonal antibody and mAb12 indicates monoclonal antibody 12 with HIC process in Table 6.

TABLE 5

Understanding of HIC viral clearance process

| Retrospective Dataset | DoE Dataset |
|---|---|
| (+) Number of mAbs (large) | (−) number of mAbs (small) |
| (−) Limited process variance | (+) Wide process variance |

TABLE 6

Apply DoE models to VC study with less than 1 LRF

| mAb | pH | Citrate (mM) | Column Loading (g/L) | Measured LRF (Log 10) | DoE Model Predicted LRF (Log 10) |
|---|---|---|---|---|---|
| mAb12 | 8.0 (high) | 30 (low-medium) | 260 (highest) | 0.48 (infectivity) 0.98 (qPCR) | 1.15 (reported LRF) 0.95 (qPCR) |

Example 6. Apply DoE to Direct the Improvement of Viral Clearance of HIC

Figure 9A:
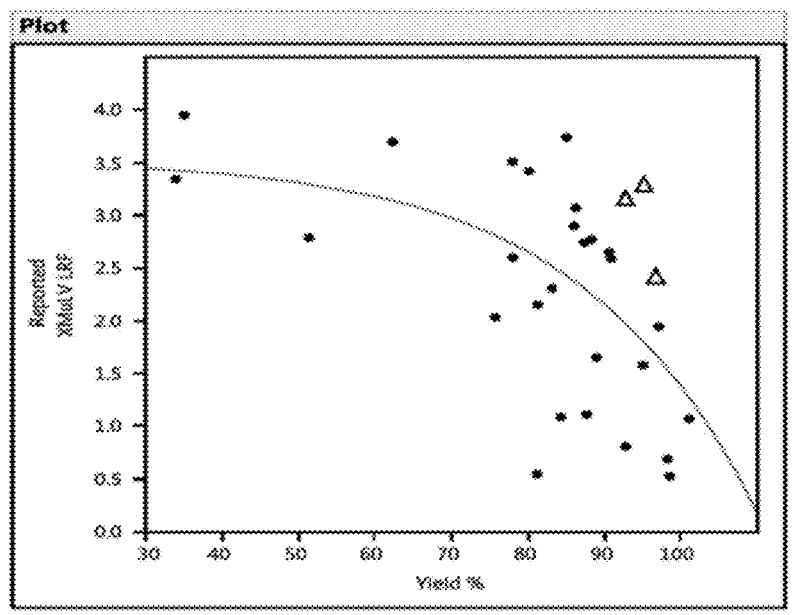
FIG. 9A shows a plot and a prediction profiler generated by applying DoE for optimizing the development factors for both yield and virus LRF by applying reported LRF models to HIC viral clearance processes according to an exemplary embodiment.
Figure 9A:
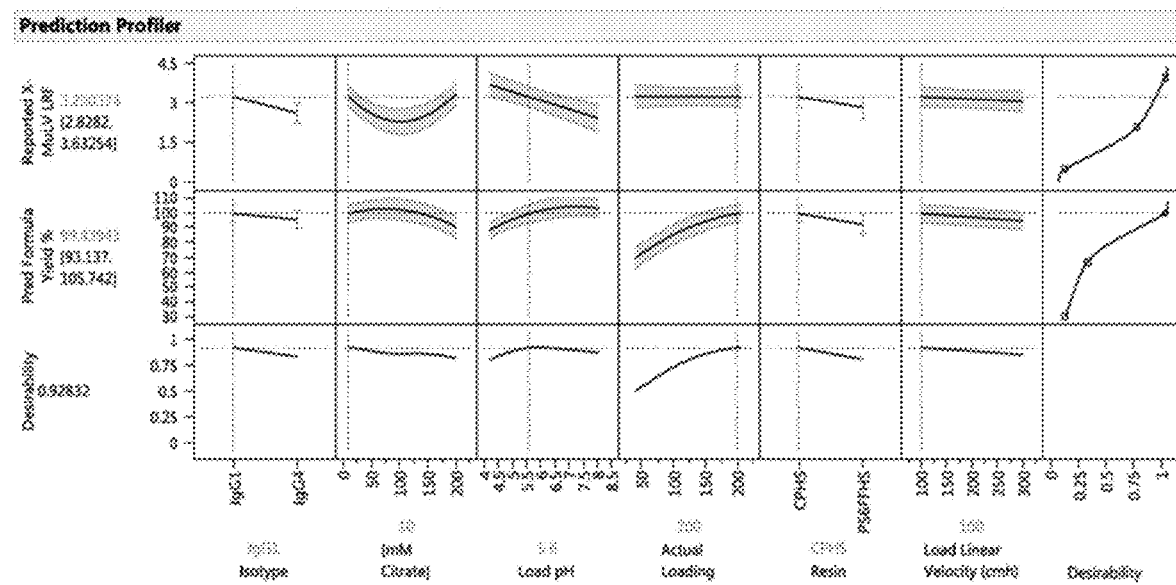

When DoE is applied, it can provide directions for optimizing the development factors toward greater improvement of HIC viral clearance processes. For example, when several LRF models were applied to HIC viral clearance processes, it achieved better viral clearance. For example, greater than 90% yield of the monoclonal antibody was achieved while providing greater than 2 LRF. The results indicate that the conditions of the development factors that resulted in high yield negative mode HIC can also achieve high virus removal. Most of the conditions which can promote adsorption of monoclonal antibodies can also promote the adsorption of X-MuLV. As shown in FIG. 9A, three observed data points have 2-3 LRF with greater than 90% yield of monoclonal antibodies, where all pH values were less than or equal to 6, citrate concentration was low at 10 mM, and the column loading was high at greater than or equal to 120 g/L.

Figure 9B:
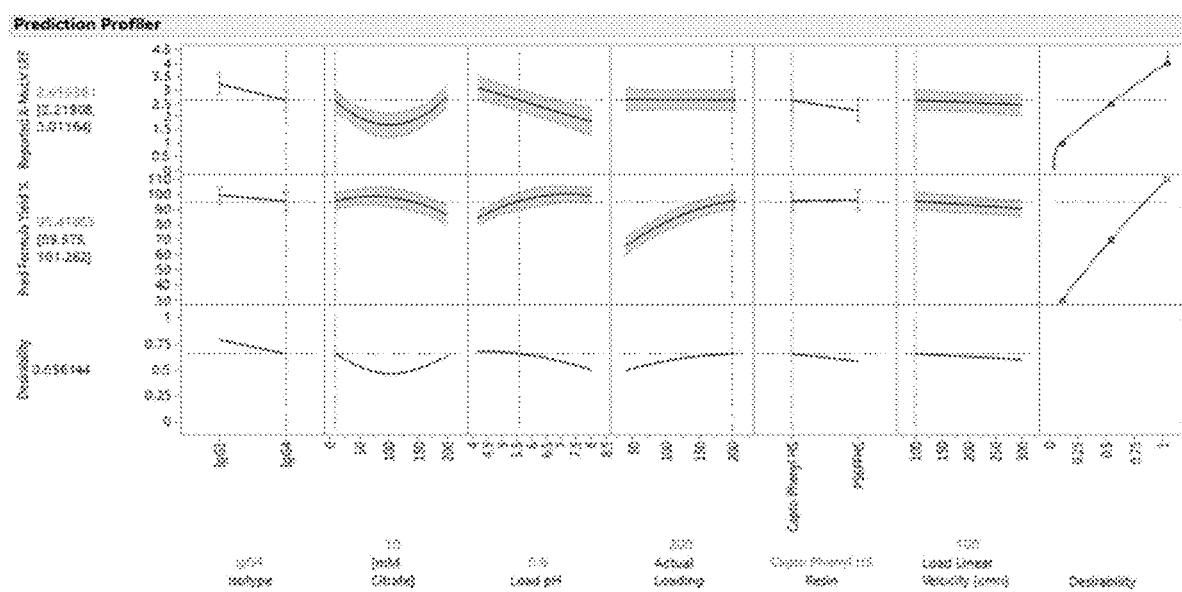
FIG. 9B shows a prediction profiler applied to IgG4 by applying DoE to provide directions for optimizing development factors for both yield and virus LRF.

FIG. 9B shows prediction profiler applied to IgG4 by applying DoE to provide directions for optimizing the development factors for both yield and virus LRF. The high yield of about 95% can still be maintained with supportive clearance of 2-3 LRF. Lower mean clearance was expected compared to IgG1, which was in-line with DoE findings.

Example 7. Relative Hydrophobicity of HIC Resins

Figure 10:
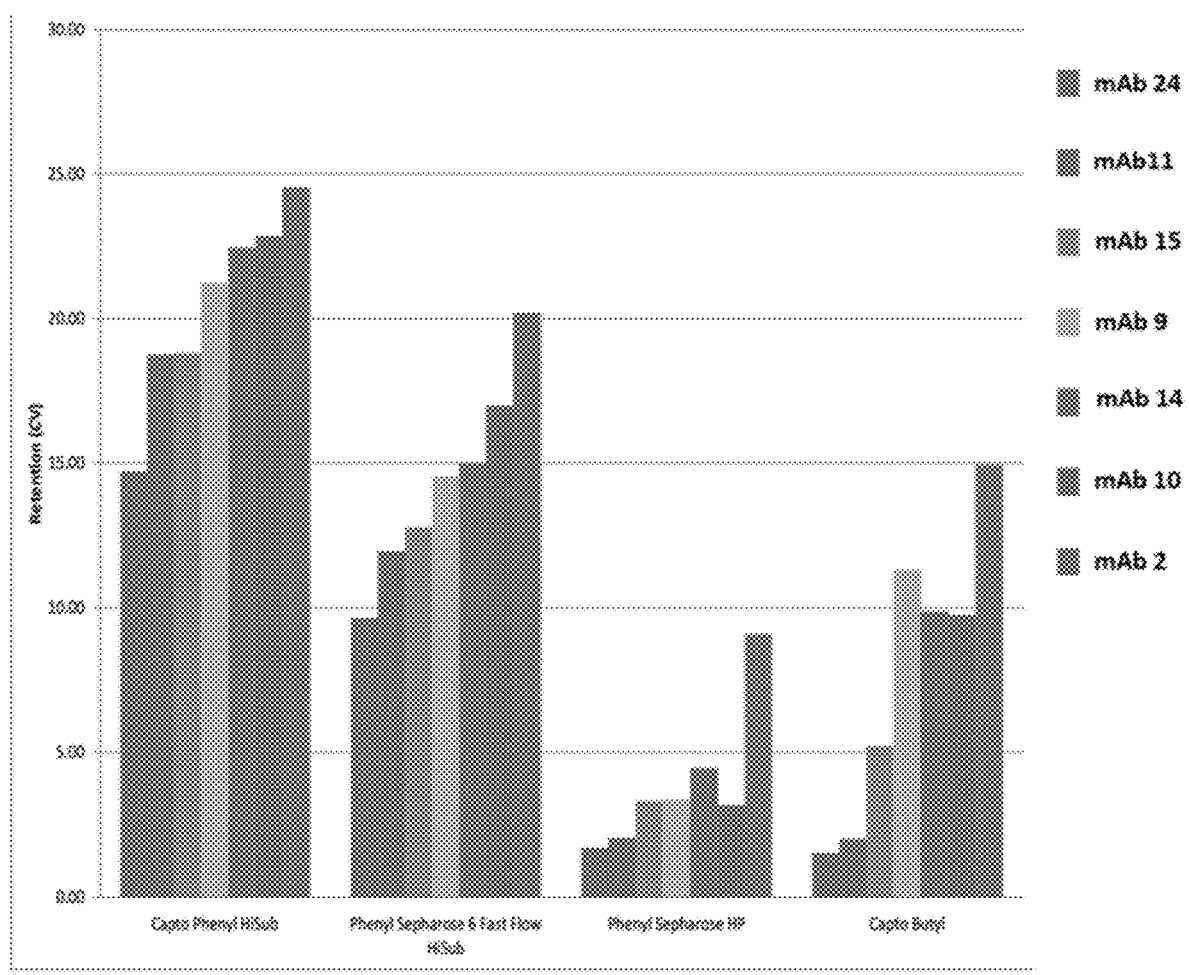
FIG. 10 shows comparisons of relative molecule hydrophobicity of several HIC resins using monoclonal antibodies (mAb) according to an exemplary embodiment.

The relative molecule hydrophobicity of several HIC resins (GE Healthcare Life Sciences) was compared using monoclonal antibodies (mAb) as shown in FIG. 10. The relative molecule hydrophobicity is comparable between capto phenyl HiSub and phenyl Sepharose 6 Fast Flow HiSub (PS6FFHS). Some reversals were observed for phenyl Sephasrose HP (low sub) and capto butyl (aliphatic). mAb2 was mostly retained in all conditions. mAb9 was not the most strongly resin retained in any condition.

Example 8. DoE Study for Viral Clearance of HIC

Figure 11:
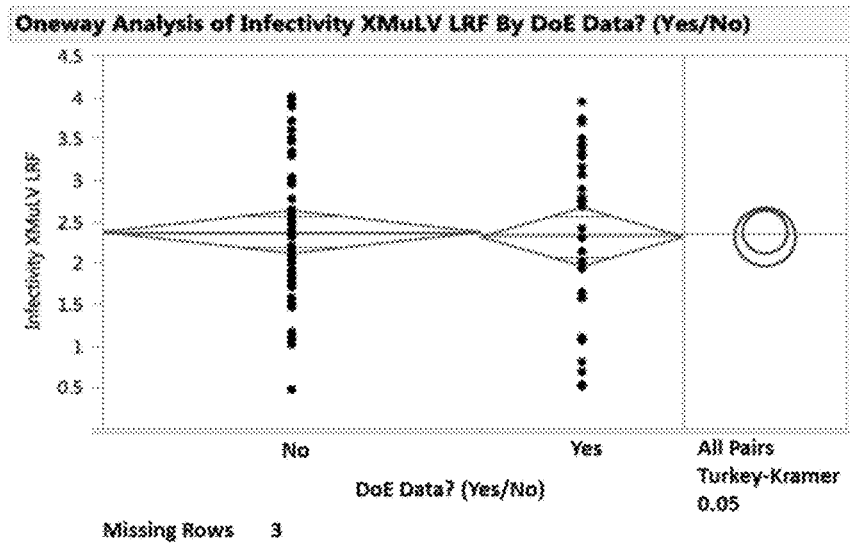
FIG. 11 shows one-way analysis of infectivity X-MuLV LRF with or without DoE data by applying DoE studies for viral clearance of HIC with various ranges of development factors according to an exemplary embodiment.
Figure 11:
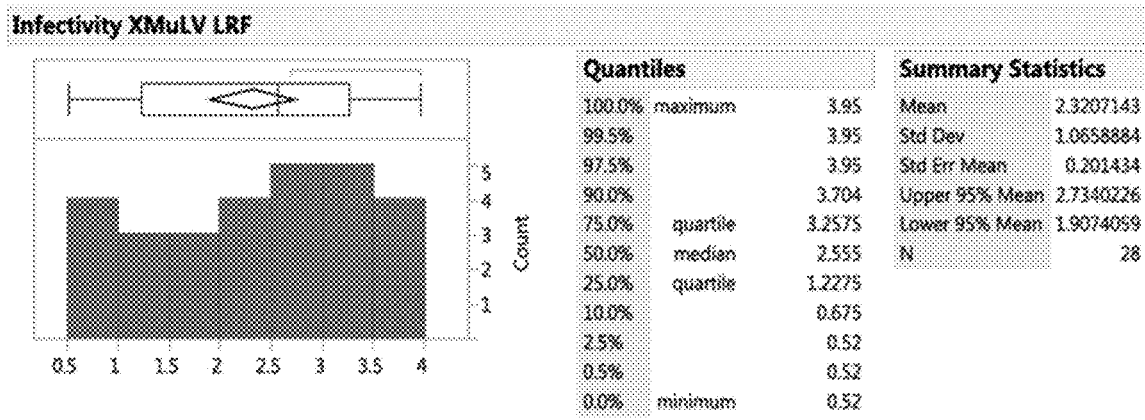
Figure 11:
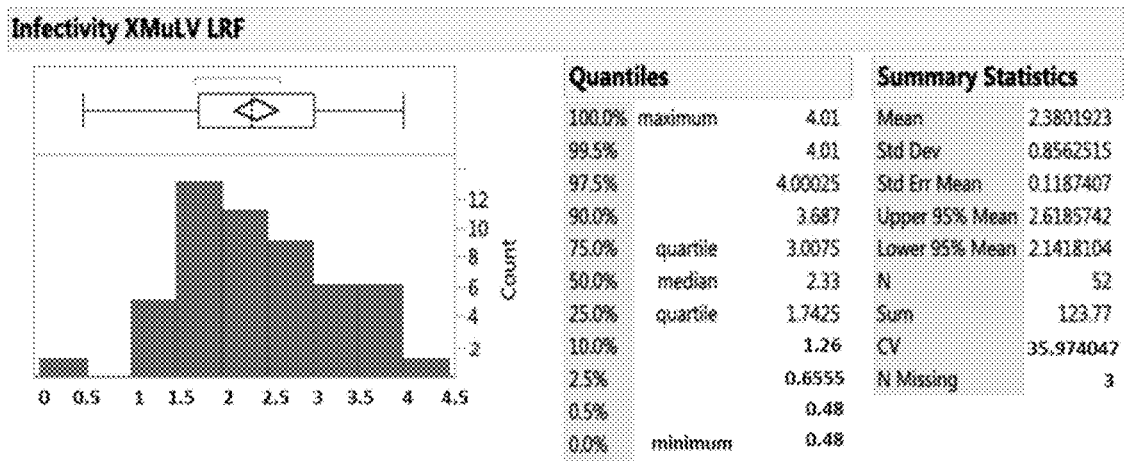

DoE studies for viral clearance of HIC with various ranges of development factors were applied to retrospective database as comparison. DoE studies for viral clearance of HIC with various ranges of development factors were applied using one-way analysis of infectivity X-MuLV LRF with or without DoE data as shown in FIG. 11. The DoE data was comparable to larger viral clearance HIC dataset, where the range of LRF values observed for DoE is in the range of 0.52-3.95 LRF, which is similar to the range of 0.48-4.01 LRF in database. The DoE data has slightly lower mean LRF with higher standard deviation (SD), which is statistically equivalent to larger viral clearance dataset as shown in FIG. 11.

The data obtained from DoE studies supports relationship between LRF by infectivity and qPCR assays. Infectivity and qPCR assays show significant comparability (R-square of 0.73) for retrospective dataset as shown in FIG. 12 using bivariate fit of infectivity X-MuLV LRF by qPCR X-MuLV LRF. The observed assay relationship can be modeled as formula (I):

Infectivity X-MuLV LRF=−0.516447+(1.6481014× qPCR X-MuLV LRF)     Formula (I)

Figure 13:
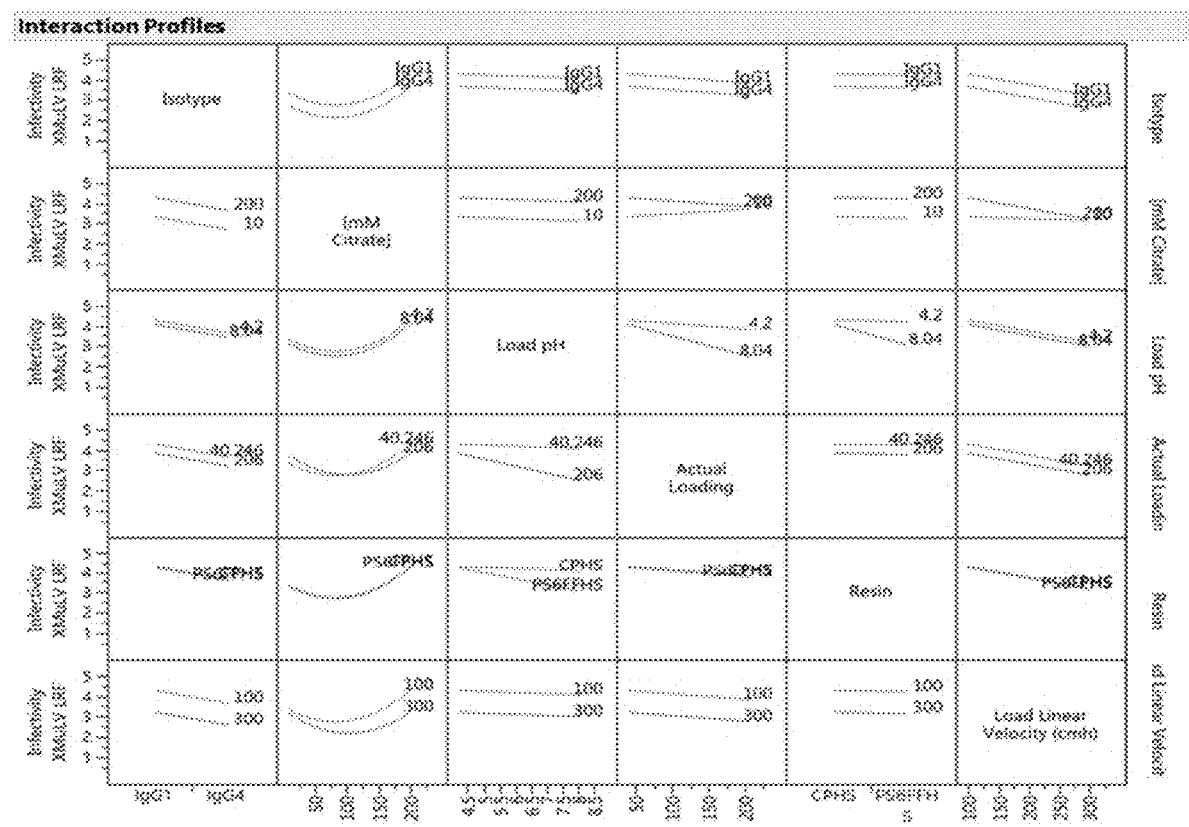
FIG. 13 shows data analysis obtained from DoE studies regarding the interaction profiler of reported HIC LRF DoE model according to an exemplary embodiment.
Figure 14A:
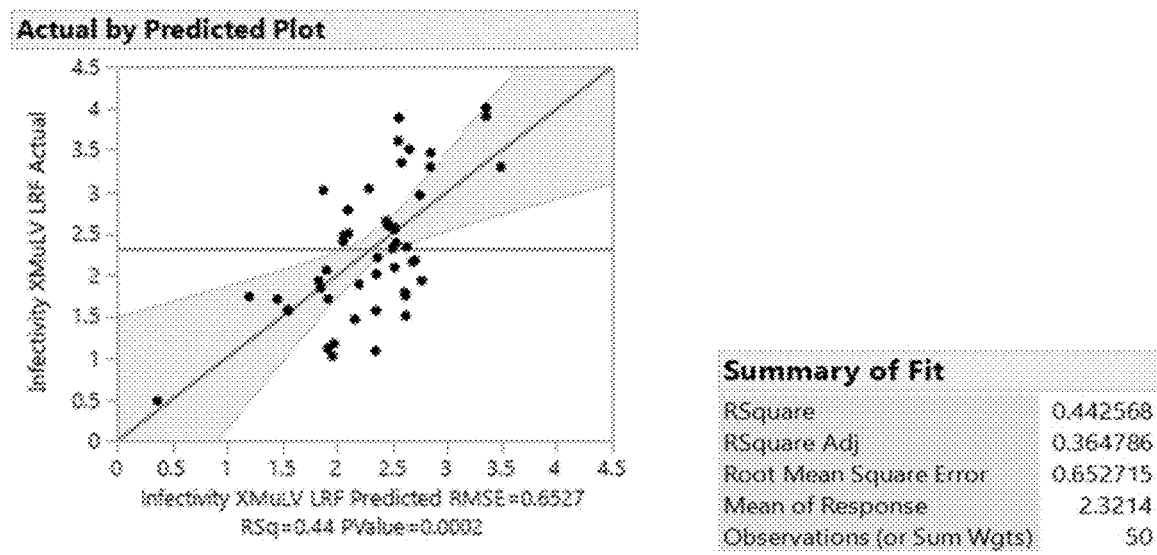
FIG. 14A shows an original model of a retrospective database for infectivity assays before the application of HIC viral clearance DoE data according to an exemplary embodiment.
Figure 14B:
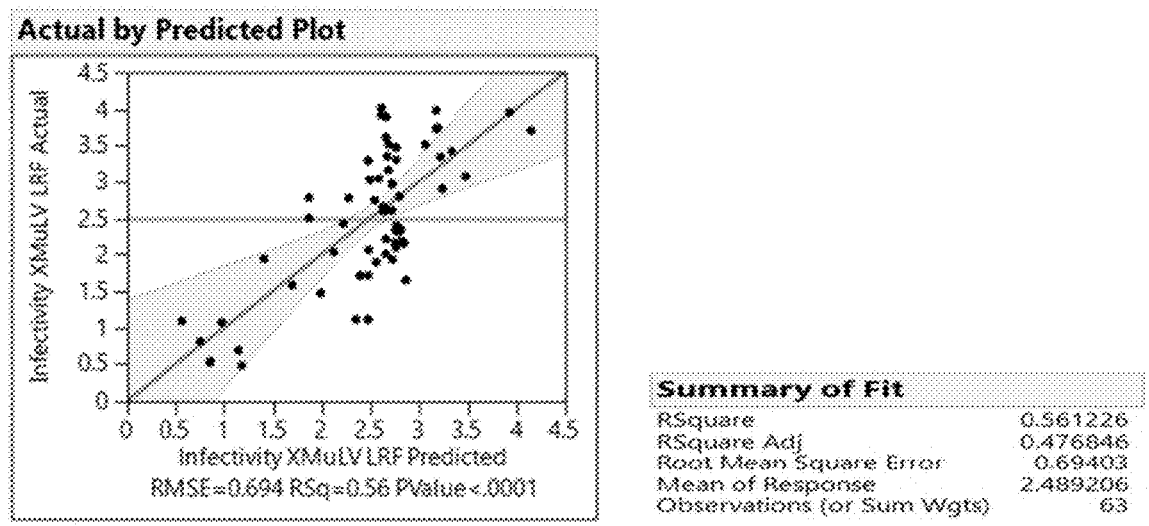
FIG. 14B shows an improved model for applying HIC viral clearance DoE data to a retrospective database for infectivity assays according to an exemplary embodiment.

The interaction profiler of reported HIC LRF DoE model is shown in FIG. 13. When HIC viral clearance DoE data was applied to retrospective database for infectivity assays, it contributed to significant model improvement by improving R-square from 0.37 to 0.48 with similar RMSE as shown in FIGS. 14A and 14B. FIG. 14A shows the original model. FIG. 14B shows the improved model by applying DoE runs. Some significant terms in the original model were dropped out. Two mechanisms, for example, inactivation and removal, were modelled.

Figure 15A:
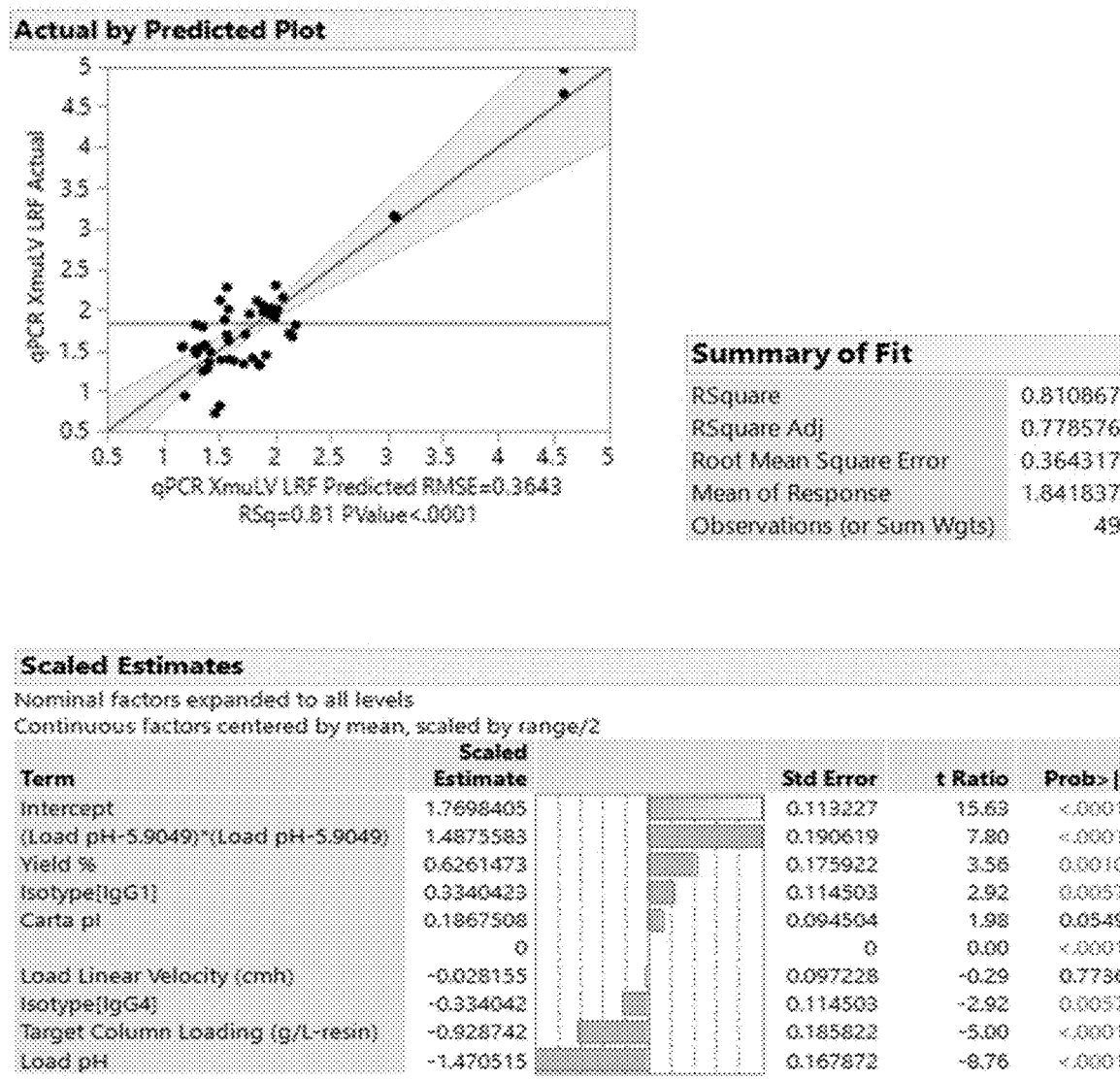
FIG. 15A shows an original model before applying HIC viral clearance DoE data to a retrospective database for a qPCR model according to an exemplary embodiment.
Figure 15B:
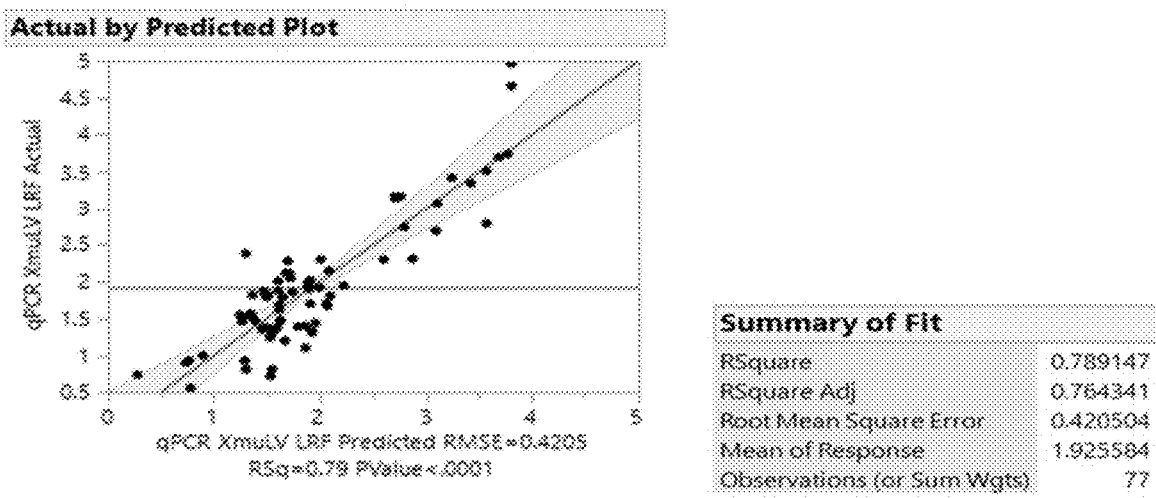
FIG. 15B shows a modified model by applying HIC viral clearance DoE data to a retrospective database for a qPCR model according to an exemplary embodiment.

When HIC viral clearance DoE data was applied to retrospective database for a qPCR model, it contributed to minimal decrease in R-square from 0.78 to 0.76 with increased RMSE from 0.36 to 0.42 as shown in FIGS. 15A and 15B. FIG. 15A shows the original model. FIG. 15B shows the modified model by applying DoE runs. DoE data supports retrospective qPCR model that is heavily influenced by three points. It was found that the development factor of load pH was the strongest factor. The design space of the modified model was filled with product-specific data which confirmed original model LRF range. It was found that it was easier to model one mechanism, such as removal.

Figure 16:
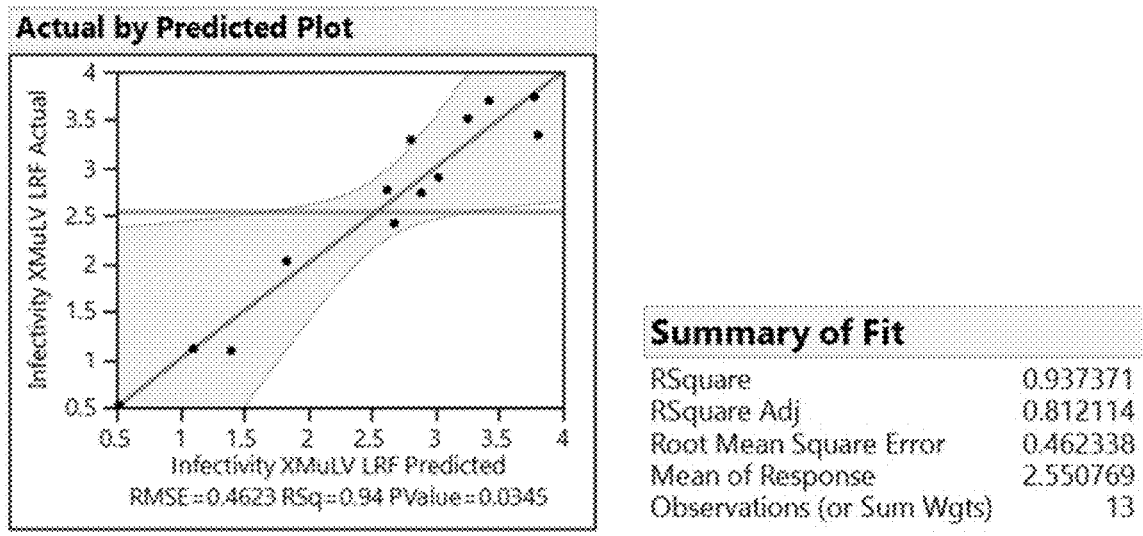
FIG. 16 shows predicted plot and scaled estimates by applying HIC viral clearance DoE data to a retrospective database for isotype IgG1 of mAb11 according to an exemplary embodiment.

HIC viral clearance DoE data was applied to retrospective database for isotype of monoclonal antibodies. The HIC DoE reported LRF by isotype of monoclonal antibody for IgG1 of mAb11 is shown in FIG. 16. FIG. 16 shows predicted plot and scaled estimates by applying HIC viral clearance DoE data to retrospective database for isotype IgG1 of mAb11 according to an exemplary embodiment. The modified model has significant model fit with higher RMSE compared to total DoE model. It was found that only the development factors of load pH and citrate are significant. The mean response of 2.6 LRF in modified model is higher than total DoE dataset at 2.3 LRF.

Figure 17:
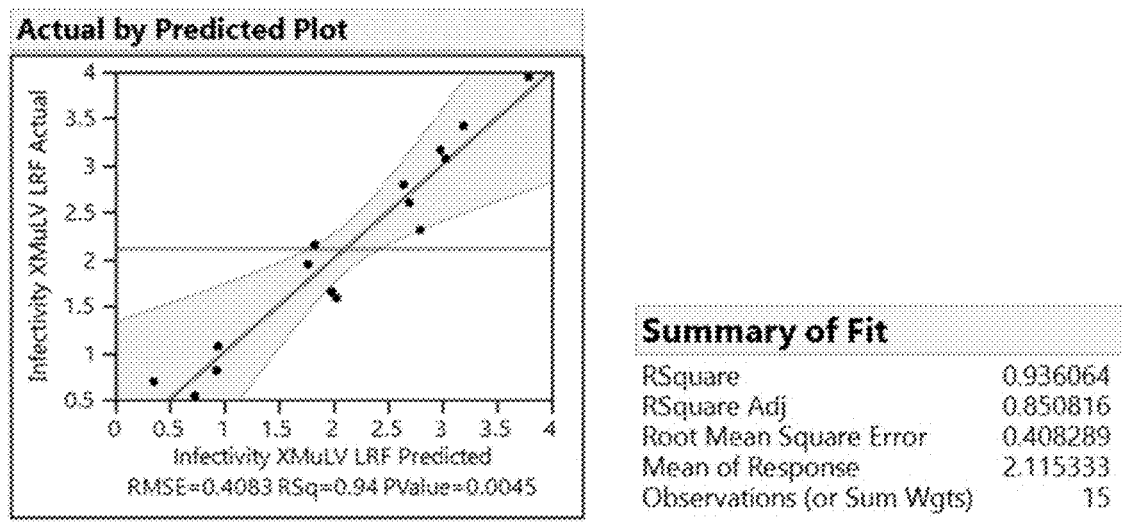
FIG. 17 shows predicted plot and scaled estimates by applying HIC viral clearance DoE data to a retrospective database for isotype IgG4 of mAb14 according to an exemplary embodiment.

HIC viral clearance DoE data was applied to retrospective database for isotype of monoclonal antibodies. The HIC DoE reported LRF by isotype of monoclonal antibody for IgG4 of mAb14 is shown in FIG. 17. FIG. 17 shows predicted plot and scaled estimates by applying HIC viral clearance DoE data to retrospective database for isotype IgG4 of mAb14 according to an exemplary embodiment. The modified IgG4 model has more sensitivity compared to IgG1 model with lower mean LRF (2.1 vs 2.6 log 10). It was found that the load pH and citrate quadratic have largest estimates. The different structures between IgG4 and IgG1 may allow for virus binding due to weaker partitioning. The relevant contributing mechanisms may include specific properties of monoclonal antibodies, such as hydrophobicity, aggregate score, or molecular charge.

Figure 18A:
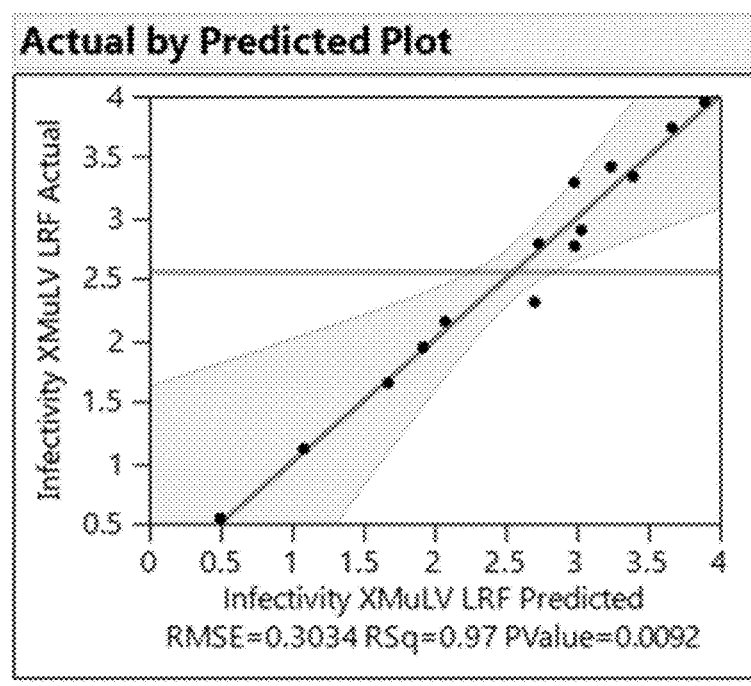
FIG. 18A shows a predicted plot by applying HIC viral clearance DoE data to a retrospective database for capto phenyl HS according to an exemplary embodiment.
Figure 18B:
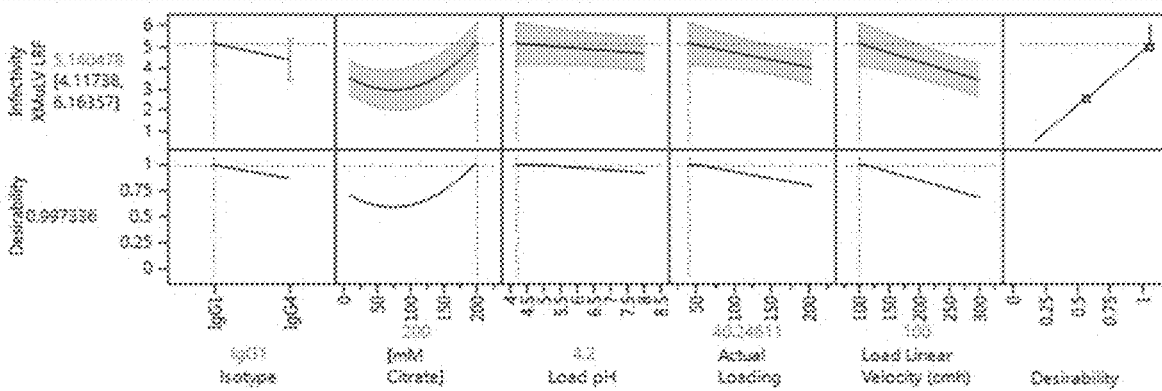
FIG. 18B shows parameter estimates and a predicted profiler by applying HIC viral clearance DoE data to retrospective database for capto phenyl HS according to an exemplary embodiment.

HIC viral clearance DoE data was applied to retrospective database for different type of resins. The HIC DoE reported LRF by resin for capto phenyl is shown in FIGS. 18A and 18B. FIG. 18A shows predicted plot by applying HIC viral clearance DoE data to retrospective database for capto phenyl according to an exemplary embodiment. FIG. 18B shows parameter estimates and predicted profiler by applying HIC viral clearance DoE data to retrospective database for capto phenyl according to an exemplary embodiment. The results indicate strong model fit with R-square greater than 0.9. The significance of isotype of monoclonal antibody is same as the results shown previously, where IgG4 is the worst-case.

Figure 19A:
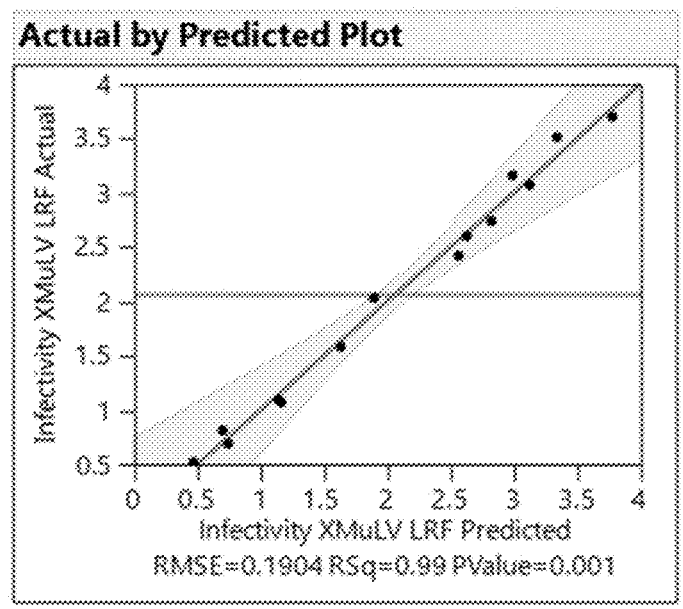
FIG. 19A shows a predicted plot by applying HIC viral clearance DoE data to a retrospective database for phenyl Sepharose 6 FF HS according to an exemplary embodiment.
Figure 19B:
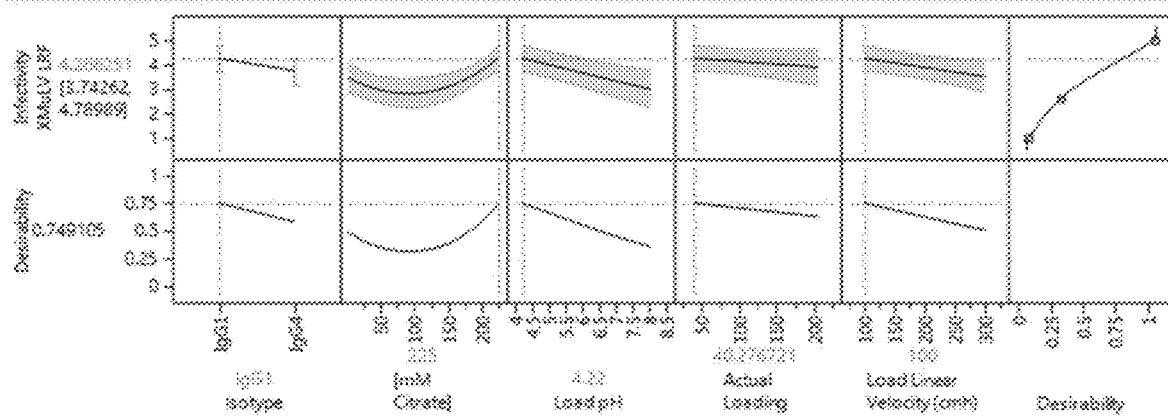
FIG. 19B shows parameter estimates and a predicted profiler by applying HIC viral clearance DoE data to a retrospective database for phenyl Sepharose 6 FF HS according to an exemplary embodiment.

HIC viral clearance DoE data was applied to retrospective database for different type of resins. The HIC DoE reported LRF by resin for phenyl Sepharose 6 FF HS is shown in FIGS. 19A and 19B. FIG. 19A shows predicted plot by applying HIC viral clearance DoE data to retrospective database for phenyl Sepharose 6 FF HS according to an exemplary embodiment. FIG. 19B shows parameter estimates and predicted profiler by applying HIC viral clearance DoE data to retrospective database for phenyl Sepharose 6 FF HS according to an exemplary embodiment. The results indicate strong model fit with R-square greater than 0.95 and low RMSE at 0.19. The mean LRF is about 0.5 log 10 which is lower than capto phenyl model (2.1 vs 2.6 log 10). The development factors of load pH and antibody isotype have largest effect size.

Example 9. Applying HIC DoE Yield Model

Figure 20:
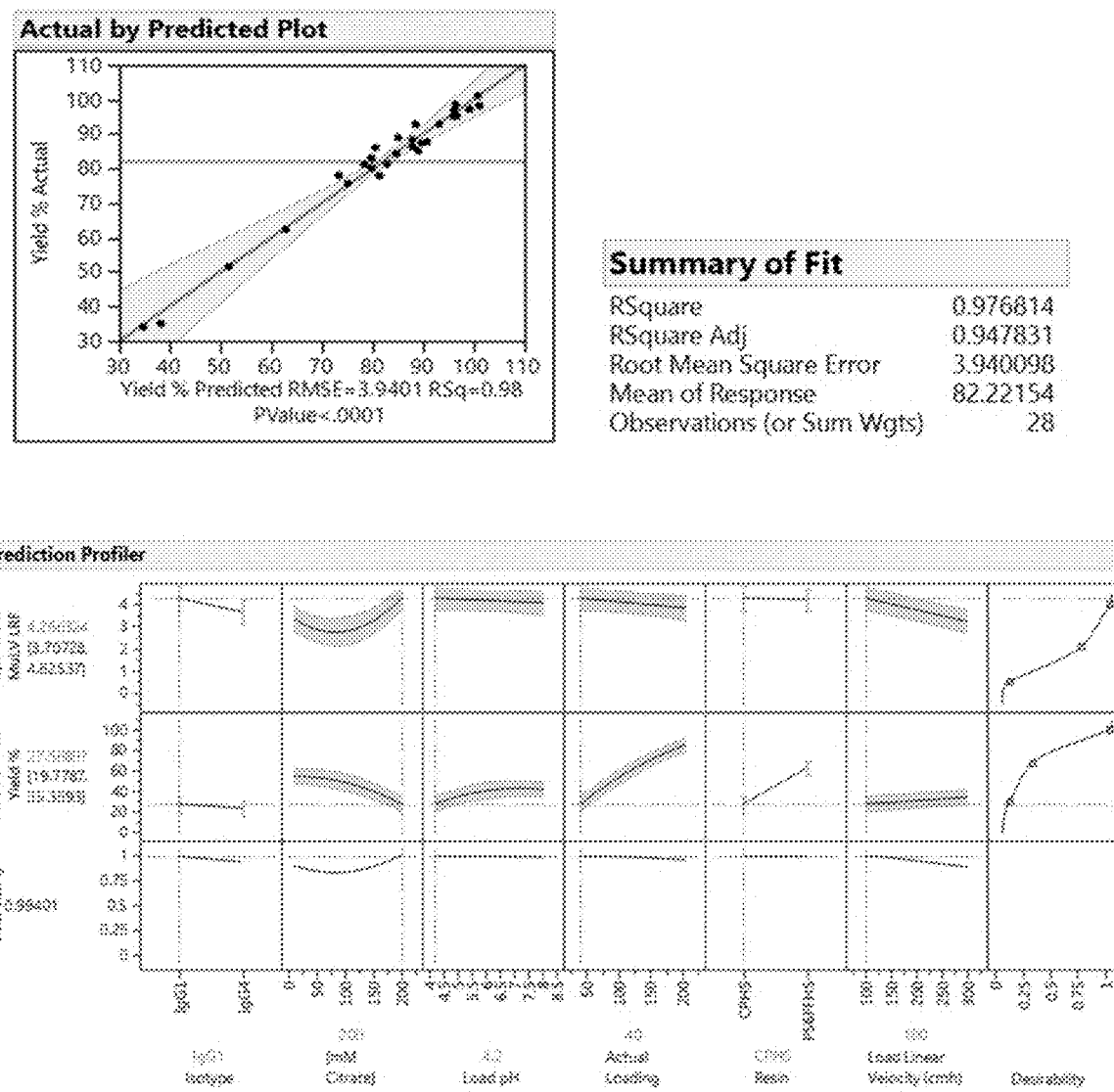
FIG. 20 shows a predicted plot and prediction profiler optimizing for yield by applying HIC DoE yield model to monitor the trend between LRF and yield according to an exemplary embodiment.

HIC DoE yield model was applied to monitor the trend between LRF and yield as shown in FIG. 20. FIG. 20 shows predicted plot and prediction profiler by applying HIC DoE yield model to monitor the trend between LRF and yield according to an exemplary embodiment. It was found that the application of HIC DoE yield model indicated an inverse trend between LRF and yield. Large ranges of development factors were relative to typical design phase of HIC DoEs. The wide yield response at 34-101% was relative to retrospective dataset at 80-100%. The maximization of HIC X-MuLV LRF at 4.3 log 10 may lead to step yield at 28%. The conditions that promoted extensive adsorption of monoclonal antibodies may also promote extensive adsorption of X-MuLV. The results indicate that virus binds to resin under the condition which also drives adsorption of monoclonal antibody to HIC, since the hydrophobic sites of the virus may be potentially exposed during the HIC process.

What is claimed is:

1. A method of purifying an antibody from a sample comprising one or more impurities including viral particles, the method comprising the steps of:
   providing the sample comprising the antibody produced in a host-cell;
   adding a sodium citrate buffer to the sample to produce a loading sample, wherein a concentration of the sodium citrate buffer is from about 10 mM to about 200 mM, and wherein adding the sodium citrate adjusts a hydrophobicity of the viral particles in the loading sample;
   adjusting a pH of the loading sample to a range of from about 4.2 to about 8.0 by adjusting an amount of sodium citrate buffer;
   loading the loading sample to a hydrophobic interaction chromatography (HIC) column to produce an HIC treated sample, wherein a concentration of the antibody in the loading sample is from about 40 g/L to about 200 g/L;

collecting the HIC treated sample; and measuring a presence of viral genomic copies or viral particles in the collected HIC treated sample.

2. The method of claim 1, wherein a resin of the HIC column is phenyl resin or a resin having an equivalent hydrophobic strength.

3. The method of claim 1, wherein a resin of the HIC column is capto-phenyl resin or a resin having an equivalent hydrophobic strength.

4. The method of claim 1, wherein a hydrophobic strength of the HIC column is within a range having a lower bound corresponding to a hydrophobic strength of phenyl resin and an upper bound corresponding to a hydrophobic strength of phenyl capto phenyl resin.

5. The method of claim 1, wherein the antibody is a monoclonal antibody or a bispecific antibody.

6. The method of claim 1, wherein the antibody has an IgG1 isotype or an IgG4 isotype.

7. The method of claim 1, wherein a flow rate through the HIC column has a linear velocity of about 100 cm/hr to about 300 cm/hr.

8. The method of claim 1, further comprising measuring a presence of viral genomic copies.

9. The method of claim 1, further comprising measuring a presence of viral particles.

10. The method of claim 1, further comprising measuring a presence of both viral genomic copies and viral particles.

11. A method of purifying an antibody from a sample comprising one or more impurities including viral particles, the method comprising the steps of:

providing the sample comprising the antibody produced in a host-cell;

adjusting a hydrophobicity of the viral particles to produce a loading sample;

adjusting a pH of the loading sample to a range of from about 4.2 to about 8.0;

loading the loading sample to a hydrophobic interaction chromatography (HIC) column to produce an HIC treated sample, wherein a concentration of the antibody in the loading sample is from about 40 g/L to about 200 g/L;

collecting the HIC treated sample;

measuring a presence of viral genomic copies or viral particles in the collected HIC treated sample; and identifying, using a D-Optimal design of experiment generated by a computer algorithm, a significant development factor from a plurality of factors, wherein the D-optimal design of experiment is optimized for removal of viral genomic copies or viral particles.

12. The method of claim 11, wherein the plurality of factors comprises:

the pH of the loading sample, a type of HIC column, the concentration of the antibody in the loading sample, a linear velocity of a flow rate through the HIC column, and a hydrophobic strength of the HIC column within a range having a lower bound corresponding to a hydrophobic strength of phenyl resin and an upper bound corresponding to a hydrophobic strength of capto phenyl resin.

13. The method of claim 12, wherein the D-Optimal design of experiment further evaluates:

an isotype of the antibody.

14. The method of claim 11, wherein the antibody is a monoclonal antibody or a bispecific antibody.

15. A method of purifying an antibody from a sample comprising one or more impurities including viral particles, the method comprising the steps of:

providing the sample comprising the antibody produced in a host-cell;

adding a sodium citrate buffer to the sample to produce a buffered sample, wherein a concentration of the sodium citrate buffer is from about 10 mM to about 200 mM, and wherein adding the sodium citrate buffer to the sample modulates adsorption of the viral particles to a hydrophobic interaction chromatography (HIC) column;

adjusting a pH of the buffered sample to a range of from about 4.2 to about 8.0 by adjusting an amount of sodium citrate buffer in the buffered sample to produce a loading sample;

loading the loading sample to a hydrophobic interaction chromatography (HIC) column to produce an HIC treated sample, wherein a concentration of the antibody in the loading sample is from about 40 g/L to about 200 g/L;

collecting the HIC treated sample;

measuring a presence of viral genomic copies or viral particles in the collected HIC treated sample; and identifying, using a D-Optimal design of experiment generated by a computer algorithm, a significant development factor from a plurality of factors, wherein the D-optimal design of experiment is optimized for removal of viral genomic copies or viral particles.

16. The method of claim 15, wherein the D-Optimal design of experiment evaluates the following factors:

the pH of the loading sample, a type of HIC column, the concentration of the antibody in the loading sample, a linear velocity of a flow rate through the HIC column, and a hydrophobic strength of the HIC column within a range having a lower bound corresponding to a hydrophobic strength of phenyl resin and an upper bound corresponding to a hydrophobic strength of capto phenyl resin.

17. The method of claim 15, wherein the antibody is a monoclonal antibody or a bispecific antibody.

18. The method of claim 16, wherein the D-Optimal design of experiment further evaluates:

an isotype of the antibody.

19. The method of claim 11, wherein the HIC column comprises phenyl resin or capto phenyl resin.

20. The method of claim 15, wherein the HIC column comprises phenyl resin or capto phenyl resin.

21. The method of claim 1, wherein measuring a presence of viral genomic copies or viral particles in the collected HIC treated sample comprises an infectivity assay, a quantitative PCR assay, or a combination thereof.

22. The method of claim 11, wherein measuring a presence of viral genomic copies or viral particles in the collected HIC treated sample comprises an infectivity assay, a quantitative PCR assay, or a combination thereof.

23. The method of claim 15, wherein measuring a presence of viral genomic copies or viral particles in the collected HIC treated sample comprises an infectivity assay, a quantitative PCR assay, or a combination thereof.

24. The method of claim 11, wherein a flow rate through the HIC column has a linear velocity of about 100 cm/hr to about 300 cm/hr.

\* \* \* \* \*